United States Patent [19]

Ferek-Petric et al.

[11] Patent Number: 5,243,976
[45] Date of Patent: Sep. 14, 1993

[54] TRICUSPID FLOW SYNCHRONIZED CARDIAC ELECTROTHERAPY SYSTEM WITH BLOOD FLOW MEASUREMENT TRANSDUCER AND CONTROLLED PACING SIGNALS BASED ON BLOOD FLOW MEASUREMENT

[76] Inventors: Bozidar Ferek-Petric, Sovinec 17; Branko Breyer, Prilaz JNA 79, both of 41000 Zagreb, Yugoslavia

[21] Appl. No.: 674,607

[22] Filed: Mar. 25, 1991

[30] Foreign Application Priority Data

Sep. 11, 1990 [YU] Yugoslavia ............ 1717/90

[51] Int. Cl.⁵ .................................. A61N 1/365
[52] U.S. Cl. ............................. 607/6; 607/19
[58] Field of Search ................... 128/419 PG

[56] References Cited

U.S. PATENT DOCUMENTS

| | | | |
|---|---|---|---|
| 3,903,897 | 9/1975 | Woollons et al. | 128/419 |
| 3,938,502 | 2/1976 | Bom | 128/2 V |
| 3,942,534 | 3/1976 | Allen et al. | 128/419 |
| 4,249,539 | 2/1981 | Vilkomerson et al. | 128/660 |
| 4,291,707 | 9/1981 | Heilman et al. | 128/784 |
| 4,319,580 | 3/1982 | Colley et al. | 128/661 |
| 4,475,551 | 10/1984 | Langer et al. | 128/419 |
| 4,535,774 | 8/1985 | Olson | 128/419 |
| 4,572,191 | 2/1986 | Mirowski et al. | 128/419 |
| 4,614,192 | 9/1986 | Imran et al. | 128/419 |
| 4,662,377 | 5/1987 | Heilman et al. | 128/419 |
| 4,686,987 | 8/1987 | Salo et al. | 128/419 |
| 4,697,595 | 10/1987 | Breyer et al. | 128/660 |
| 4,706,681 | 11/1987 | Breyer et al. | 128/642 |
| 4,766,902 | 8/1988 | Schroeppel | 128/419 |
| 4,766,905 | 8/1988 | Namekawa | 128/663 |
| 4,768,911 | 9/1988 | Balter | 414/3 |
| 4,768,912 | 9/1988 | Miura | 414/32 |
| 4,770,177 | 9/1988 | Schroeppel | 128/419 |
| 4,771,788 | 9/1988 | Millar | 128/661 |
| 4,771,789 | 9/1988 | Namekawa | 128/661 |
| 4,773,401 | 9/1988 | Citak et al. | 128/419 |
| 4,774,950 | 10/1988 | Cohen | 128/419 |
| 4,779,617 | 10/1988 | Whigham | 128/419 |
| 4,790,317 | 12/1988 | Davies | 128/419 |
| 4,790,322 | 12/1988 | Iinuma | 128/661 |
| 4,790,323 | 12/1988 | Leavitt et al. | 128/661.09 |
| 4,791,931 | 12/1988 | Slate | 128/419 |
| 4,802,481 | 2/1989 | Schroeppel | 128/419 |
| 4,802,490 | 2/1989 | Johnston | 128/661.08 |
| 4,917,115 | 4/1990 | Flamming | 128/419 PG |
| 4,936,304 | 6/1990 | Kresh et al. | 128/419 PG |
| 4,967,749 | 11/1990 | Cohen | 128/419 PG |
| 5,003,976 | 4/1991 | Alt | 128/419 PG |
| 5,031,615 | 7/1991 | Alt | 128/419 PG |
| 5,058,583 | 10/1991 | Geddes et al. | 128/419 PG |

FOREIGN PATENT DOCUMENTS 0311019  4/1989  European Pat. Off.

Primary Examiner—William E. Kamm
Attorney, Agent, or Firm—Hill, Steadman & Simpson

[57] ABSTRACT

A cardiac electrotherapy system has flow velocity measurement capability for measuring a velocity of blood flow at a region of a tricuspid valve of a heart. A pacing system is provided which outputs a pacing electrical signal to the heart. A control unit which is responsive to a measured flow velocity from the flow velocity measurement unit detects heart irregularities and controls electrical pacing signals to the heart. In detecting heart irregularities, peak flow velocity waveforms are detected and analyzed. The flow velocity measurement employs a Doppler ultrasonic transducer which is mounted on a cardiac pacing lead in spaced relation to a pacing electrode at a distal end of the lead. When the pacing lead is inserted in the heart, the pacing electrode is placed at an apex of the right ventricle and the piezoelectric Doppler transducer is positioned at or near the tricuspid valve. The flow velocity transducer is preferably formed as an annular piezo body having associated electrodes. An ultrasonic lens directs ultrasonic rays from the transducer and an ultrasonic wave inhibitor structure prevents transmission of ultrasonic waves in an undesired direction. With the cardiac electrotherapy system disclosed, improved and more reliable monitoring of cardiac activity is achieved and a corresponding improved pacing results.

53 Claims, 17 Drawing Sheets

TRICUSPID FLOW SYNCHRONIZED CARDIAC ELECTROTHERAPY SYSTEM WITH BLOOD FLOW MEASUREMENT TRANSDUCER AND CONTROLLED PACING SIGNALS BASED ON BLOOD FLOW MEASUREMENT

BACKGROUND OF THE INVENTION

This invention relates to cardiac electrotherapy, and particularly to measurement of blood flow velocity characteristics within the heart and large blood vessels for the purpose of control of the electrotherapy.

Physiologic cardiac pacing is very important on a temporary as well as on a permanent basis. Temporary pacing is usually applied either after cardiac surgery or during myocardial infarction because of the transient conduction disturbance or arrhythmia. Patients at rest have significantly improved cardiac output when ventricular contraction is synchronous with atrial filling of ventricles. This is very important for faster recovery after surgery or myocardial infarction. Furthermore, some arrhythmias like supraventricular tachycardias and extrasystolies may be prevented by means of physiologic pacing.

Patients with chronic conduction and rhythm disturbance have to receive a permanent implantable pacing system. They also have a significant contribution of atria to the hemodynamic benefit. There are two basic modes of physiologic cardiac pacing: sequential and synchronous. The sequential atrio-ventricular pacing is used to restore normal atrio-ventricular relationships. In this mode an atrium and a ventricle are paced by twin stimuli separated by an appropriate physiologic interval. However, the heart rate is controlled by the pacemaker program and does not vary according to the physiological needs. The synchronous cardiac pacing approximates most closely to the normal cardiac rhythm. The spontaneous atrial electrogram (P-wave) is sensed by an electrode usually in contact with the atrial endocardium. This is used to trigger the ventricle after an appropriate preset delay. Because the atrial rhythm is paced by our natural pacemaker sinus-atrial node, the frequency varies naturally according to the body workload. Therefore, the P-wave synchronous ventricular cardiac pacing is considered to be the most physiologic rate-responsive pacing.

There is a significant drawback of physiologic pacing systems which complicates the surgical procedure in comparison with non-physiologic pacing. The physiologic pacing requires the implantation of two leads: one atrial and one ventricular. Modern dual-chamber pacemakers have the ability to switch from sequential to synchronous pacing and vice versa according to the atrial rhythm which is monitored in the atrial channel. If the patient has a normal function of the sinus node and atria, the atrial lead is only used to sense the atrial activity and the ventricular lead is used to sense the ventricular activity and to pace the ventricles. Because the sensing of atrial activity may be done by an electrode floating within the right atrial cavity, a lot of effort has been done to design a single pass lead for P-wave synchronous ventricular pacing comprising the atrial and ventricular electrode on the same lead. Such a system has been described in U.S. Pat. No. 3,903,897. However, the atrial electrogram has a significantly lower amplitude when sensed by a floating electrode in comparison with an electrode having a direct contact with the atrial muscle. Therefore, such systems have to have a high sensitivity amplifier in the atrial channel. As a consequence, the high susceptibility on far fields appears, causing more likely occurrence of the various oversensing phenomena. Furthermore, many patients have a low amplitude atrial electrogram and therefore the atrial undersensing is more frequent in such systems. The system described in the European Patent No. 311,019 monitors ventricular impedance continuously using an electrode in the ventricle without requiring additional sensing in the atrium. A detected impedance waveform can be used to trigger ventricular stimulus synchronously with atrial filling of the ventricle. In this system, the impedance changes because of the ventricular volume change caused by the atrial filling.

Very important to technical and clinical performance of P-wave synchronous pacemakers is the upper rate behavior. A maximum pacing rate of ventricles is limited and therefore the atrial rhythm tracking by the ventricles will happen within the specified frequency range. The maximum tracking rate has to be a programmable parameter in order to tailor the pacing frequency range according to the patient's needs. Those who suffer from angina pectoris and impaired ventricular function are not capable of tolerating high tracking rates, while those with a healthy cardiac muscle can tolerate high rate ventricular pacing. The synchronous pacing can be impaired by the atrial undulation and fibrillation when the pacemaker sustains the maximum tracking rate during high atrial pathologic rhythm. therefore, even the intermittent atrial fibrillation is a contraindication for synchronous pacing. Patients suffering from intermittent atrial fibrillation would benefit a lot from a pacemaker comprising a reliable atrial fibrillation detector and which could switch from synchronous to rate responsive pacing in the case of atrial fibrillation occurrence and vice versa, and switch back to the synchronous mode upon the fibrillation termination. It would be very important that a pacemaker could monitor the ventricular performance and adapt the maximum tracking rate in such a way as to prevent angina and high-rate induced ischemia. It would be also important that a pacemaker could discriminate premature ventricular contractions with compensatory pause from those without the compensatory pause. Tachycardia is a condition in which the heart beats rapidly. Pathologic tachycardia is the one which disturbs the hemodynamics causing the drop of systemic blood pressure. There are many types of pathologic tachycardias, and the electrophysiology differentiates two major classes: supraventricular and ventricular tachycardias. Tachycardia is often the result of electrical feedback within the heart structures where the natural beat results in the feedback of an electrical stimulus which prematurely triggers another beat. There are several different cardiac pacing modes which may terminate the tachycardia. The underlying principle in all of them is that if a pacemaker stimulates the heart at least once shortly after a heartbeat (and before the next naturally occurring heartbeat at the rapid rate), the interposed stimulated heartbeat disrupts the stability of the feedback loop, thus reverting the tachycardia to sinus rhythm. Such a pacemaker was disclosed in U.S. Pat. No. 3,942,534 which, following detection of tachycardia, generates a stimulus after a delay interval.

The most hazardous arrhythmia is ventricular tachycardia which may progress into lethal arrhythmia ventricular fibrillation. Because the ventricular tachycardia is not always successfully treated and terminated by antitachycardia pacing, the implantable cardioverter-defibrillator is used to deliver a high energy pulse shock in order to cause the cardioversion of ventricular tachycardia to sinus rhythm. Such an implantable device was disclosed in U.S. Pat. No. 4,614,192 comprising a bipolar electrode for R-wave sensing, the system utilizing heart rate averaging and a probability density function for fibrillation detection. The similar system for a cardioversion is disclosed in U.S. Pat. No. 4,768,512 which has the high frequency pulse delivery. All these systems deliver high energy shock through special patch-electrodes such as described in U.S. Pat. No. 4,291,707. In order to simplify the surgical procedure, systems comprising a superior vena cava electrode and a subcutaneous electrode, such as described in U.S. Pat. No. 4,662,377, have been developed. The supraventricular tachycardia caused by atrial flutter or fibrillation can be also treated by an implantable cardioverter, such as described in U.S. Pat. No. 4,572,191.

The difficulty in the electrotherapy treatment of tachycardia is that the implantable apparatus has to comprise means for the accurate detection of pathologic tachycardia in order to deliver the electrotherapy pulses whenever the pathologic tachycardia occurs. The problem is that the heart rhythm increases its frequency physiologically whenever either physical or emotional stress occurs. The means for pathologic tachycardia detection must accurately differentiate the natural sinus tachycardia which should not be treated by means of electrotherapy, from the pathologic tachycardia which has to be treated. Therefore, the discrimination between normal and pathologic tachycardia on the basis of frequency measurement is not reliable. In order to overcome this problem, numerous methods of tachycardia detection have been developed which are applicable in the implantable electrotherapy devices.

Such a system has been disclosed in U.S. Pat. No. 4,475,551 where the heart rate sensing as well as the probability density function are used to distinguish between ventricular fibrillation and high rate tachycardia. A more sophisticated system has been disclosed in U.S. Pat. No. 4,790,317 which can automatically recognize the pathologic rhythm by means of monitoring of the pulse sequence representing the ventricular electrical activity. At least two sensing positions, i.e. to each ventricular epicardial surface, are used, but more sensing points will obtain better discrimination between normal and pathologic rhythms.

The problems which may occur with such systems are that they are susceptible to electromagnetic interference and muscular noise, as well as improper gain of the heart beat detectors causing the undersensing of cardiac rhythm. Therefore, some means for detecting of noise and for automatic sensitivity adjustment is desirable. Therefore, the implanted pacemaker noise rejection system described in the U.S. Pat. No. 4,779,617, as well as the automatic sensitivity control systems disclosed in U.S. Pat. Nos. 4,766,902 and 4,768,511 have been developed.

The implantable cardioverting system usually comprises the cardiac pacing system because of the backup of bradycardial events which follow the cardioversion high voltage pulse. There are also patients who suffer from pathologic tachycardia as well as from bradycardia, which have to be treated by cardiac pacing. therefore, the physiological sensor for control of the heart rate is desirable in order to obtain the rate responsive pacing. It is also possible that the cardioversion implantable device comprises a dual chamber physiologic pacing function. In such a system, a sensor for atrial fibrillation detection would be important, not only for the appropriate ventricular response on atrial rhythms, but also for differentiating supraventricular from ventricular tachycardia.

There are many physiological control systems for rate responsive pacing, but only a few of them can be used for tachycardia detection as well. As far as it is known to the inventors, none of these sensor systems can be used for ventricular tachycardia detection, rate responsive pacing, for atrial fibrillation detection, for pacing capture, and for noise detection. The system disclosed in U.S. Pat. No. 4,774,950 comprises a circulatory systematic blood pressure measurement system which detects the drop of pressure in the case of pathologic heart rhythm. A similar system is described in U.S. Pat. No. 4,791,931 where the pressure is measured by means of arterial wall stretch detection. Another system disclosed in U.S. Pat. No. 4,770,177 adjusts the pacing rate relative to changes in venous blood vessel diameter that is measured by means of a piezoelectric sensor. The heart contractions change the ventricular chamber volume due to the inflow and outflow of blood, thus varying the impedance within the chamber. The impedance measurement was used in U.S. Pat. No. 4,773,401 in order to obtain the physiological control of pacing rate. Furthermore, the stroke volume and ventricular volume measurement is possible in the system described in U.S. Pat. No. 4,686,987 as well as in U.S. Pat. No. 4,535,774. The system disclosed in U.S. Pat. No. 4,802,481 comprises a transducer which detects the opening of the tricuspid valve in order to calculate the ejection time, which is the sensor for rate responsive pacing. Obviously, all these systems measure indirectly the mechanical contraction of the heart which is the consequence of the electrical depolarization and which has the performance influenced by a sympathetic and a parasympathetic nervous system as well as by circulatory catecholamines. The sympathetic stimulation and circulatory catecholamines increase the velocity of the contraction, and therefore the hemodynamic forces are accordingly transferred to the circulatory system. In the case of pathologic rhythm having an electric depolarization disturbance, hemodynamics will be impeded. The quality of the mechanical cardiac contraction significantly differs in normal and pathologic rhythms. Not only the contraction but also the cardiac relaxation is influenced by circulatory catecholamines. In pathologic cardiac rhythm, the relaxation of the heart will be critically impeded. As far as it is known to the inventors, none of the systems used the parameters of cardiac relaxation, i.e. diastole for the cardiac electrotherapy control.

Ultrasonic measurement of blood flow has recently become an important noninvasive diagnostic method. Two methods have emerged as practical, i.e. the continuous wave (CW) and the pulsed (PW) Doppler systems. Very sophisticated and clinically useful systems have been developed such as described in U.S. Pat. No. 4,790,322 enabling automatic measuring independent to direction of ultrasonic beam emission. The ultrasonic transmitter-receiver for blood velocity measurement was described in U.S. Pat. No. 4,766,905 having improved noise reduction. Another system disclosed in U.S. Pat. No. 4,771,789 calculates and displays acceleration of a moving reflective member in an organism. A flow imaging detector for blood velocity measurement, such as disclosed in U.S. Pat. No. 4,790,323, weights samples of an auto-correlation function with reliability criterion so electrical noise dominated samples can be weighted less. All these inventions enabled the perfect imaging of the blood flow in the echocardiographic scanner image. Nevertheless, in some clinical applications, more accuracy was necessary and therefore the ultrasonic invasive methods have been introduced. An apparatus with a catheter for ultrasonic examining of hollow organs was described in U.S. Pat. No. 3,938,502. With continuing miniaturization of the apparatus, the idea of measuring blood flow or other parameters with piezoelectric transducers mounted on catheters (cardiac or other) became feasible. The localization and visualization systems have been developed which enabled the ultrasonic guidance of invasive procedures. The ultrasonic needle tip localization system was disclosed in U.S. Pat. No. 4,249,539. The ultrasonically marked catheters and cardiac pacing leads have been described in U.S. Pat. Nos. 4,697,595 and 4,706,681, respectively.

A particular problem to be solved is the measurement of the blood flow characteristics within the heart and large blood vessels. The system disclosed in U.S. Pat. No. 4,319,580 was developed to detect air emboli in the blood by using a cylindrical transducer for the detection. This approach was adequate for strongly reflective objects such as emboli and for the specified task of essentially only detecting them. The approach, however, does not yield a possibility to measure the flow characteristics as needed for pacemaker control.

Along similar lines there have been developed devices for measurement and control of large vessel blood flow estimation and cardiac output measurement as per U.S. Pat. No. 4,771,788 and U.S. Pat. No. 4,802,490. Apart from its use as a Doppler transducer, the device described in the U.S. Pat. No. 4,802,490 is from the ultrasonics point of view equal to the devices described in U.S. Pat. Nos. 4,706,681 and 4,697,595, although it has an additional flow restriction device which is immaterial in the comparison of prior art for the present application. The device described in U.S. Pat. No. 4,771,788 has basically the same ability to measure the flow by means of ultrasound, but is not suitable for implantation in the human body as a part of an electrotherapy system. This is so because it requires an additional support wire, which for different purposes may be helpful, but rules the method out for the aforementioned purposes.

Physiologic cardiac pacing is very important on temporary as well as on a permanent basis. Temporary pacing is usually applied either after cardiac surgery or during myocardial infarction because of the transient conduction disturbance or arrhythmia. Patients in rest have significantly improved cardiac output when ventricular contraction is synchronous with atrial filling of ventricles. This is very important for faster recovery after surgery or myocardial infarction. Furthermore, some arrhythmias like supraventricular tachycardias and extrasystolies may be prevented by means of physiologic pacing.

SUMMARY OF THE INVENTION

An object of the present invention is to provide a pacemaker which will, in normal atrial rhythm, act in a synchronous mode and maintain atrio-ventricular synchronism, yet with the need for implantation of a single lead.

It is an object of the present invention to provide a pacemaker comprising sensors for rate responsive ventricular pacing.

It is a further object of the present invention to provide a pacemaker comprising a reliable means for atrial fibrillation detection and which will maintain the rate responsive pacing while the atrial fibrillation is sustained.

It is another object of the present invention to provide a cardiac pacemaker which will monitor the right ventricular filling dynamics in order to estimate the ventricular muscle performance, and which will automatically reprogram the maximum tracking rate in such a way as to prevent angina pectoris and high-rate induced myocardial ischemia.

It is a further object of the present invention to provide a pacemaker capable of detecting premature ventricular contractions without, as well as with, compensatory pause.

It is another object of this invention to provide a pacemaker capable of confirming ventricular capture.

It is also an object of this invention to provide a pacemaker capable of discriminating sinus tachycardia from pathologic tachycardia.

According to the invention, flow characteristics are measured for pacemaker control. The blood flow along a blood vessel or within the heart is monitored with a device for blood flow velocity measurement mounted on a cardiac pacing lead.

With the invention, the flow waveform through the tricuspid valve is used for synchronization and control of ventricular cardiac pacing.

Also, according to the invention, the blood flow along the blood vessel or within the heart is monitored with a Doppler system using piezoelectric transducers mounted on a cardiac pacing lead.

Also in the invention, an ultrasound beam shaping and tilting device which positively controls the direction of Doppler measurements with an added accuracy and reliability is provided.

DESCRIPTION OF THE PREFERRED EMBODIMENTS

Figure 1:
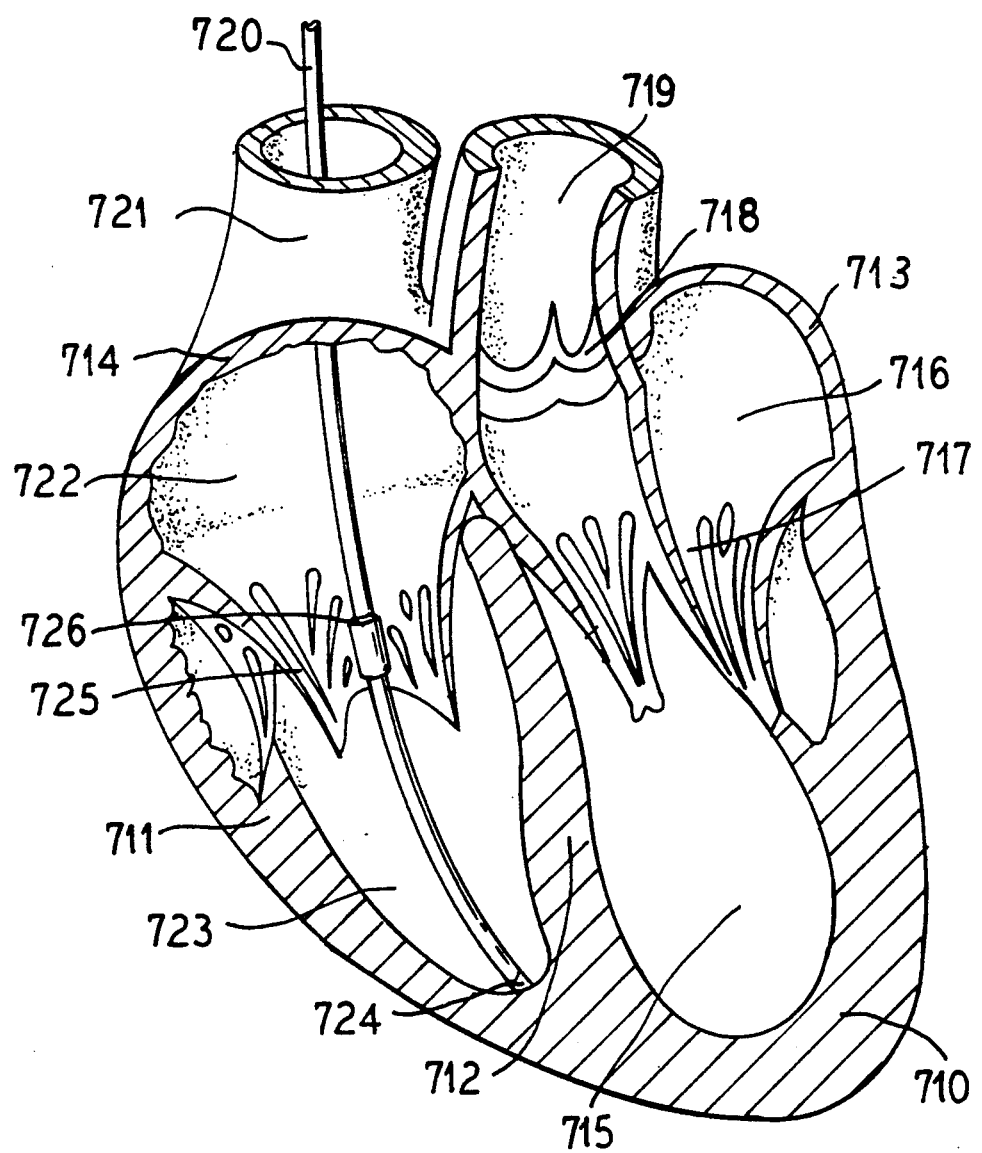
FIG. 1 is a cross-sectional four chamber view of the human heart showing approximately the anatomic structures and a cardiac pacing lead comprising a device for blood flow velocity measurement implanted in the right heart.

In the embodiment of FIG. 1, the pulsed wave flow measurement pacing lead is shown within the anatomic structures of the human heart. The heart is disclosed in the four chamber cross-section, and the myocardial cross-section is visible for the left-ventricular wall 710, the right-ventricular wall 711, the interventricular septrum 712, the left-atrial wall 713 and the right-atrial wall 714. Two chambers of the left heart, left ventricle 715 and left atrium 716 are separated by the mitral valve 717. The left ventricular outflow tract consists of the aortic valve 718 and aorta 719. A cardiac pacing lead 720 is implanted through the vena cava superior 721 and the right atrium 722 in the right ventricle 723, with its pacing electrode 724 located in the apex of the right ventricle. In the lower right-atrial region, in the proximity of the tricuspid valve 725, the lead 720 comprises a flow velocity measurement assembly 726. Because the lead is bent in the rhythm of cardiac contractions, it is important that the flow velocity measurement device is designed in such a way as to prevent the distortion of the tricuspid flow waveform pattern caused by movements of the lead itself. There are several methods of flow velocity measurement. The ultrasonic methods of either Doppler or phase shift are very accurate and are long-term stable, but because of high current drain, these are intended to be used in external devices. The flow measurement device may be also a pressure gradient type sensor. It may be also a device which measures the capacitance change in the vicinity of the tricuspid valve. Very accurate is the electromagnetic type flowmeter. The thermal transport flow transducers may also be used. However, despite the method used, the pacing control principle remains the same as it is shown in the following figures.

Figure 2:
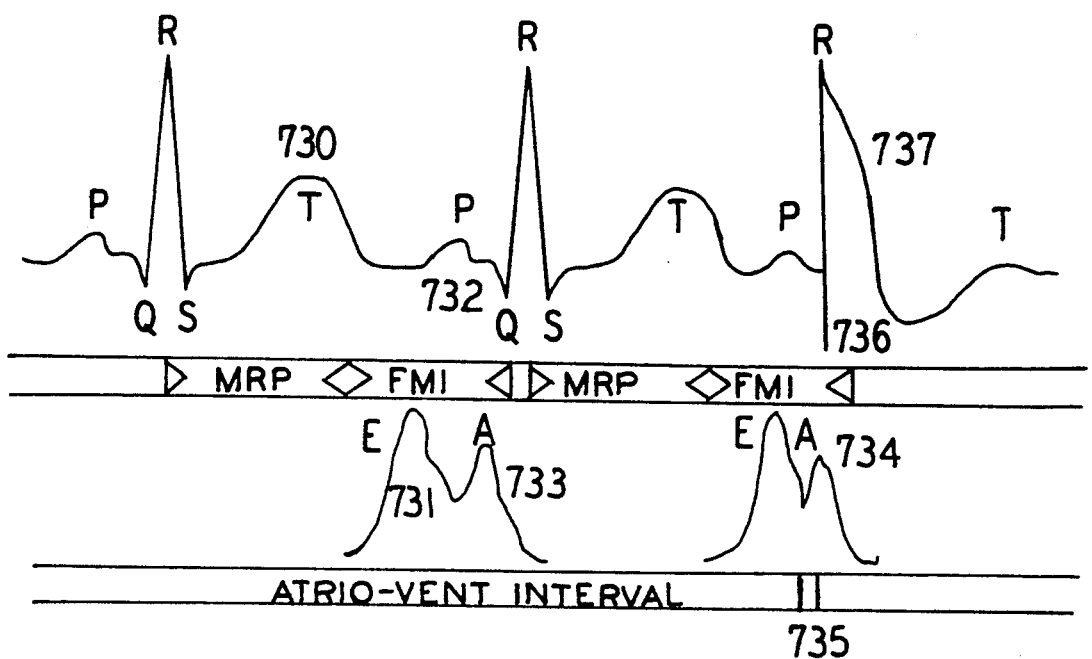
FIG. 2 is an illustration of a typical waveform of the blood flow velocity measurement through the tricuspid valve, relative to the electrocardiogram in normal atrial function.

In the embodiment of FIG. 2 an example of the electrocardiogram and corresponding tricuspid flow waveform is disclosed. P waves, QRS complexes and T waves are designated, illustrating a normal ECG. The flow velocity waveform through the tricuspid valve is disclosed under the ECG in time correlation to the ECG. Important timing intervals are designated like measurement refractory period MRP, flow velocity measurement interval FMI and atrio-ventricular interval. Every sensed or paced ventricular event initiates the flow velocity measurement refractory period which is followed by the flow velocity measurement interval. These intervals are inversely proportional to the heart frequency. After the repolarization of the heart which caused the T wave 730, the relaxation of the heart muscle causes the early diastolic filling wave 731 having the peak blood velocity E. The following atrial depolarization causes the P wave 732 and corresponding atrial muscle contraction which pumps the additional blood quantity producing the blood flow wave 733 having peak velocity A. The ratio of peak velocities E/A is a hemodynamic parameter showing the cardiac muscle performance. A similar waveform is obtained when measuring the mitral valve flow where peak velocities have greater values (on the order of 1 m/s) in comparison with the tricuspid valve velocities which are half slower. Another hemodynamic parameter being used in clinical practice is the ratio of the time integrated wave E and the time integrated wave A. The example is given for the healthy human heart, but pathologic conditions may disturb these relationships. This is used in this invention for diagnostic purposes. First of all, synchronized pacing is obtained in this invention by means of sensing the flow velocity A wave and synchronizing the ventricular pacing with it, and not with the endocardial P wave, as it is done in conventional VDD pacing systems. This is illustrated in the last complex of the disclosed ECG strip where the subsequent A-wave 734 is sensed and the atrio-ventricular interval 735 is initiated (shown as a black bar). At the end of the A-V interval, the pacing impulse 736 is generated producing the paced R-wave 737. It is obvious that A-V intervals in this system are much shorter than in systems which sense the atrial electrogram. In the case of severe ventricular arrhythmia like ventricular fibrillation, E waves disappear because the missing ventricular contraction causes missing ventricular relaxation. Ventricular tachycardia will produce an irregular peak velocity of E waves having a significantly lower magnitude of that in normal ventricular contraction. A decrease of peak velocity magnitude is dependent on the tachycardia frequency. This is used for reliable life threatening arrhythmias detection. Any ischemic episode like pacing induced high rate ischaemia will change the ratio of peak velocities as well as the ratio of time integrals. This is used for physiological maximum tracking rate response to prevent angina pectoris. The E/A ratio is significantly decreased in the case of ventricular premature contraction without the compensatory pause, which enables the exact detection and counting of the premature ventricular contractions.

Figure 3:
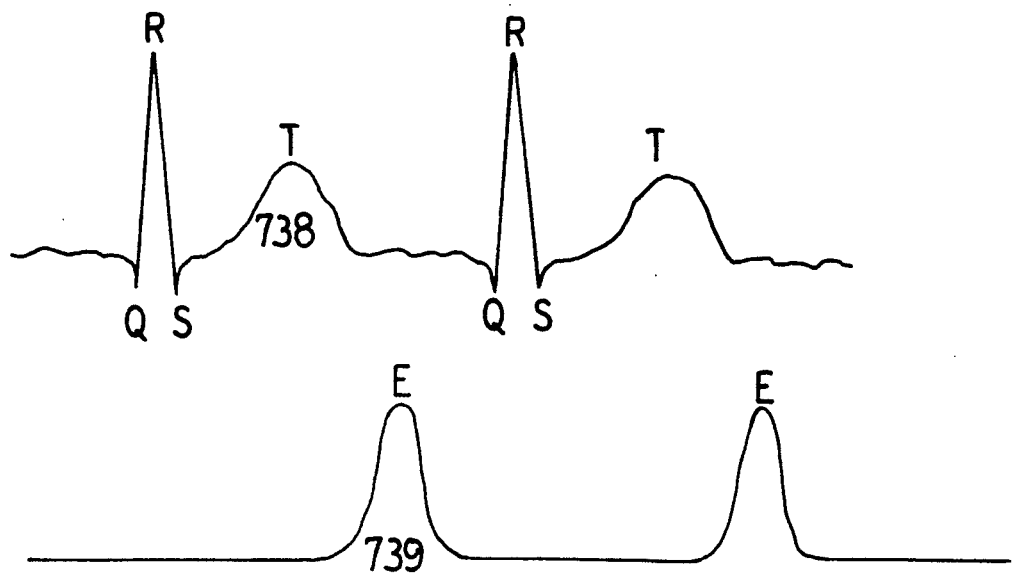
FIG. 3 is an illustration of a typical waveform of the blood flow velocity measurement through the tricuspid valve, relative to the electrocardiogram in atrial fibrillation.

In the embodiment of FIG. 3, an example of the electrocardiogram and corresponding tricuspid flow waveform is disclosed. QRS complexes and T waves are designated, illustrating the atrial fibrillation rhythm. The flow velocity waveform through the tricuspid valve is disclosed under the ECG in time correlation to the ECG waveform. The QRS complex is proceeded by a T-wave 738 which represents the cardiac repolarization. The consequence of the cardiac muscle relaxation is an early diastolic filling wave 739 having a peak velocity E. Because of the atrial fibrillation, there is no atrial filling wave as in the previous figure. This example shows how an easy and reliable detection of atrial fibrillation may be done, which is actually the detection of the disappearance of the atrial filling wave.

Figure 4:
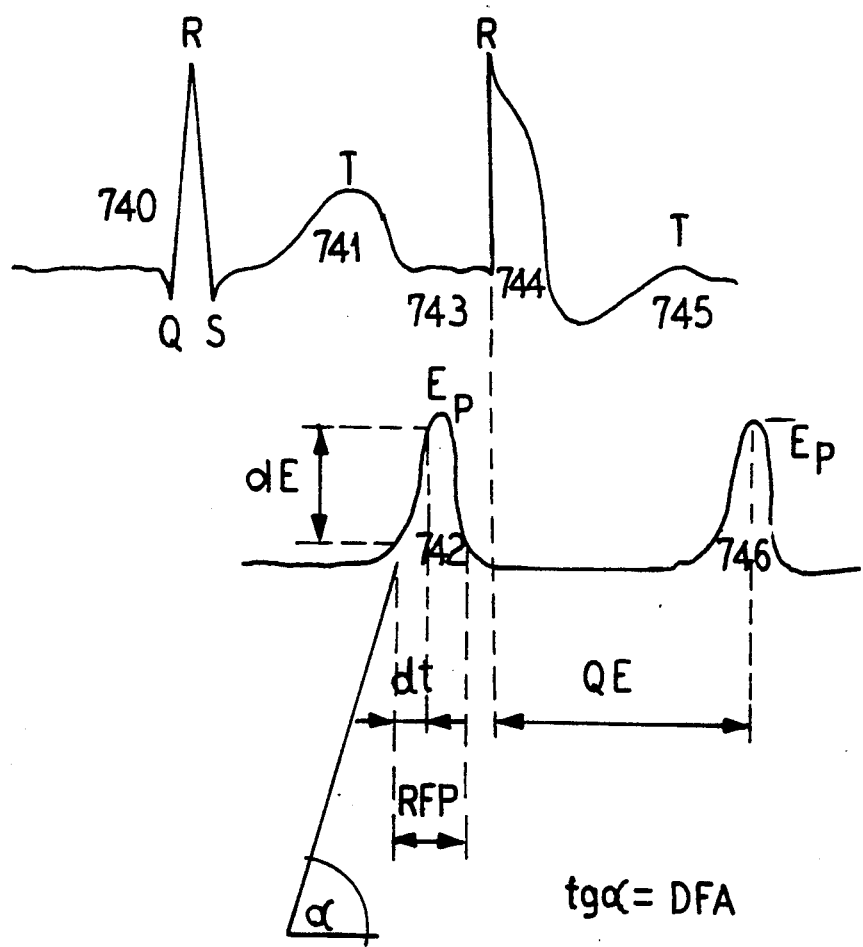
FIG. 4 is an illustration of the measurements of the flow velocity waveform to obtain rate responsive pacing sensors.

In the embodiment of FIG. 4, there is disclosed the ECG strip with a corresponding tricuspid flow velocity waveform in atrial fibrillation rhythm when the rate responsive pacing is necessary. This figure is an example of measurements which have to be done on both waveforms, i.e. ECG and tricuspid flow waveforms, in order to obtain the sensors for rate responsive pacing. Circulatory catecholamines directly influence the interval between the QRS complex and the corresponding following E wave, as well as influencing the rate of diastolic filling. Therefore, the sensors for rate responsive pacing are available in this system. The QRS complex 740 is followed by a T-wave 741. As a consequence of the cardiac muscle repolarization, the relaxation occurs causing the E-wave 742 in the tricuspid flow waveform. The pacemaker spike 743 produces the stimulated QRS complex 744 and consequently the proceeding T-wave 745 causes another E-wave 746. The peak velocity $E_p$ of the rapid filling is continuously measured for every heart beat. The rapid filling period RFP which is the E-wave duration, is measured as well as the first derivative of the E-wave onset which is the diastolic filling acceleration DFA. Also, the interval QE between the pacemaker spike and the E-wave onset is measured. In the case of exercise, the circulatory catecholamines concentration increases and the peak velocity $E_p$ of diastolic filling increases as well as the diastolic filling acceleration, while the QE interval and the rapid filling period will be shortened. The adequate algorithms within the microprocessor of the implanted device will process the above mentioned measured data in such a way as to physiologically increase the cardiac pacing rate in the case of physical exercise of a patient.

Figure 5:
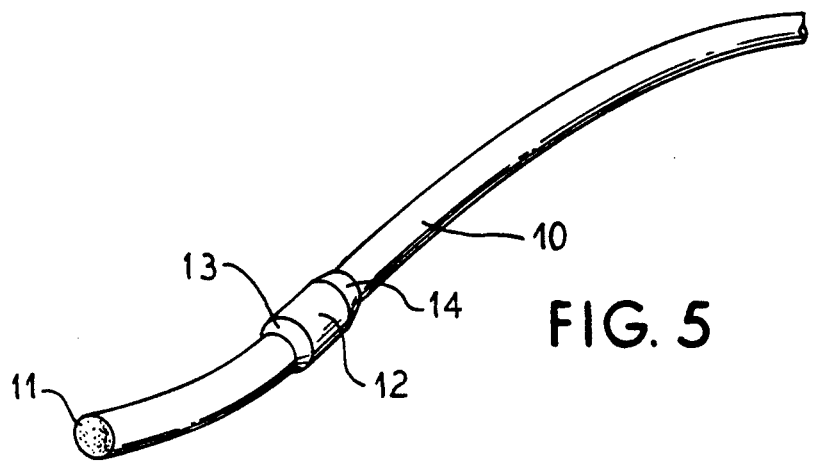
FIG. 5 is a perspective view of an unipolar cardiac pacing lead comprising an axially polarized piezoelectric transducer for pulsed wave flow measurement, with the distal part of the lead being shown.

In the embodiment of FIG. 5, a pulsed wave flow measurement cardiac pacing lead consists of a plastic body 10 having a pacing electrode on the tip. A pulsed wave flow measurement piezoelectric transducer 12 of cylindric form is built into the lead and is fixed at its surface at a distance from the tip electrode. The distance is such that, in normal operation, the transducer 12 is positioned near to and proximal to the tricuspid heart valve. There is a plastic ultrasound lens 13 positioned distally by the transducer which determines the direction of ultrasound transmission and reception. A reflective or absorptive backing 14 is fixed proximally by the transducer. The transducer is of a cylindrical form poled lengthwise and with electrodes on its top and bottom. In this way the ultrasound directivity characteristics are directed along the catheter. This particular property makes it virtually insensitive to flows in other directions than the axial direction. At the proximal end of the lead, which is not shown, there is a connector system for the connection of the lead to the electronic circuits.

Figure 6:
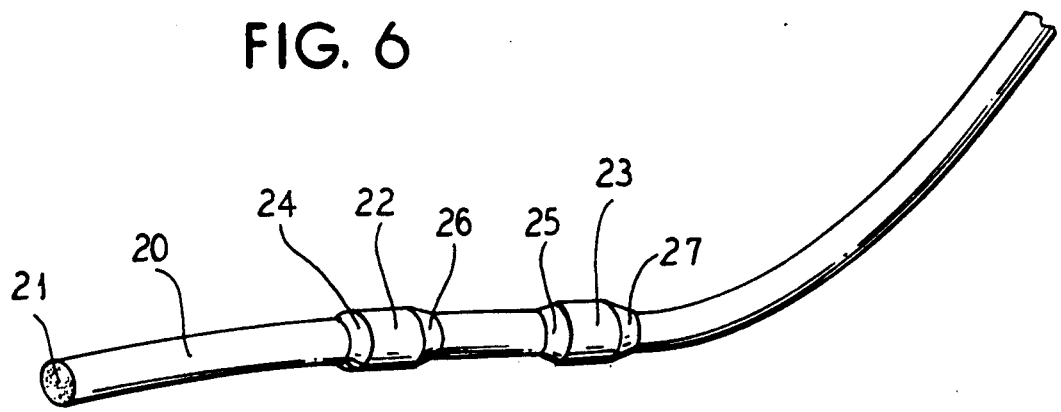
FIG. 6 is a perspective view of a unipolar cardiac pacing lead comprising a pair of axially polarized transducers for continuous wave flow measurement, showing the distal part of the lead.

In the embodiment of FIG. 6, a continuous wave flow measurement cardiac pacing lead consists of a plastic body 20 having a pacing electrode 21 on the tip. There are two piezoelectric transducers 22 and 23 mounted coaxially with the lead at a distance from the tip. The distance is such as to position the transducers 22 and 23 in the vicinity of the tricuspid heart valve. The transducers 22 and 23 are of a ring or cylindric form, with electrodes at their top and bottom (not shown) connected via built-in lead conductors (not shown) to the lead connector (not shown) at the proximal end of the lead which is not shown. The plastic ultrasound lenses 24 and 25, as well as the absorptive or reflective backings 26 and 27, control the direction of ultrasound transmission and reception respectively.

Figure 7:
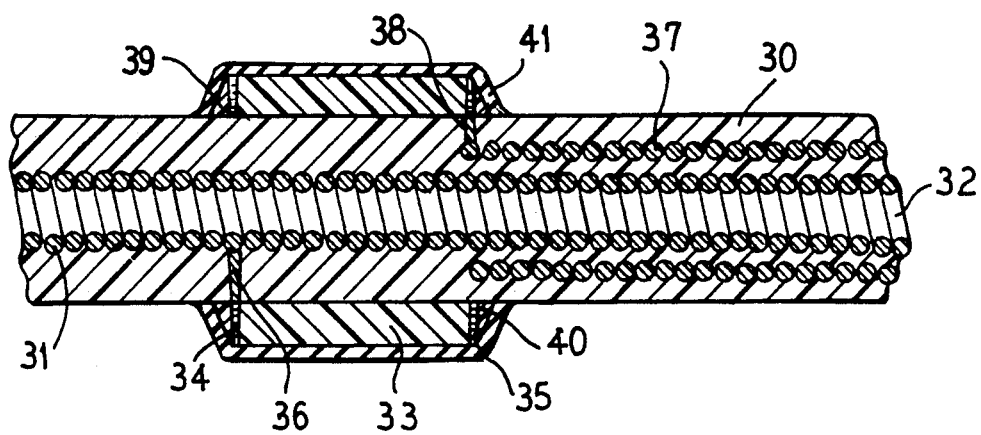
FIG. 7 is a detailed axial cross-sectional view of the segment of pacing leads from FIGS. 5 and 6 disclosing the part of the lead where the flow measurement transducer is fixed.

In the embodiment of FIG. 7 there is disclosed a detailed axial cross-section of the lead and the flow measurement transducer either from the lead from FIG. 1 or from the distal transducer of the lead from FIG. 2. Within the plastic body 30 there is a lead conductor 31 having a stylet channel 32 which connects the pacing electrode at the distal end (not shown) with the connector at the proximal end (not shown) of the lead. The cylindrical piezoelectric transducer 33, mounted coaxially on the plastic body 30, has two electrodes 34 and 35 which are co-fired at the proximal and distal end of the transducer in such a way as to pole the transducer axially. The transducer electrode 34 is electrically connected with the pacing lead conductor 31 by means of the connection bridge 36. The transducer electrode 35 is electrically connected with another lead conductor 37 by means of another connection bridge 38. An ultrasonic lens 39 is fitted and glued on the transducer. The lens 39 is of the form of a tapered ring and represents an essentially conical ultrasonic lens. At the end opposite to the lens of the transducer there is a backing 40 glued onto the electrode 35. The backing 40 is constructed of either an air equivalent material, such as expanded plastic, or of an ultrasound absorbing material, such as synthetic resin filled with metal powder. This backing is of such a tapered form that it does not obstruct the indwelling procedure. The lens 39, the transducer 33, and the backing 40 are covered with a thin sheath 41 of electrically insulating material not thicker than 5% of the ultrasound wavelength used. The disclosed lead assembly comprises helically wound coaxial lead conductors with a stylet channel which is the technology used in leads for permanent implantation. A simpler design is possible for temporary cardiac leads using ordinary insulated copper wires in a plastic tube. The plastic body may consist of multiple insulation sheaths, i.e. plastic tubes between and over the lead conductors.

Figure 8:
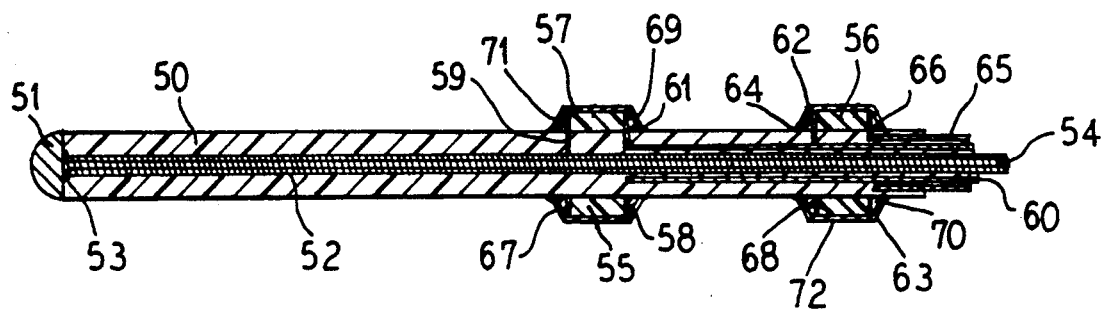
FIG. 8 is an axial cross-sectional view of the distal part of pacing lead from FIG. 6.

In the embodiment of FIG. 8, the distal part of the continuous wave flow measurement pacing lead consists of a plastic body 50 having an electrode 51 on its tip which is electrically connected to the inner lead conductor 52 by means of either conductive gluing or soldering member 53. The inner lead conductor 52 has a stylet channel 54, and on the proximal part of the lead (not shown) it is terminated with connector pin (not shown) on the connector assembly (not shown). Proximally from the tip there is a flow measurement assembly comprising two cylindric piezoelectric transducers 55 and 56 which are mounted coaxially with the plastic body 50. Transducer 55 comprises co-fired electrodes 57 and 58 which pole the transducer 55 axially. The electrode 57 is electrically connected to the inner lead conductor 52 by means of conductive bridge 59. In the same manner, the electrode 58 is connected to the middle coaxial lead conductor 60 by means of the conductive bridge 61. In the disclosed example, transducer 55 is electrically connected to the electronic circuits (not shown) through lead conductors 52 and 60 by means of said connector assembly (not shown) at the proximal end of the lead (not shown). Transducer 56 comprises co-fired electrodes 62 and 63 which pole the transducer 56 also axially. The electrode 62 is electrically connected to the middle lead conductor 60 by means of the conductive bridge 64. In the same manner, the electrode 63 is connected to the outer lead conductor 65 by means of the conductive bridge 66. In the disclosed example, transducer 56 is electrically connected to the electronic circuits (not shown) through lead conductors 60 and 65 by means of the connector assembly (not shown) at the proximal end of the lead (not shown). Ultrasonic lenses 67 and 68 are fitted to the transducer electrodes 57 and 62 respectively, and are glued. The lenses 67 and 68 are of the form of tapered rings and represent essentially conical ultrasonic lenses. At the opposite end of the transducers 55 and 56, the backings 69 and 70 are fitted to the transducer electrodes 58 and 63, and are glued. The backings are made of either an air equivalent material such as expanded plastic or of an ultrasound absorbing material such as synthetic resin filled with metal powder. Backings are of such a tapered form that they do not obstruct the indwelling procedure. The distance between transducers 55 and 56 is much larger than the ultrasound wavelength within the body tissues. The distance of the transducers 55 and 56 from the lead tip and electrode 51 is such as to enable the continuous wave flow measurement through the tricuspid valve while the electrode 51 is positioned in the apex of the right ventricle. Transducers 55 and 56, lenses 67 and 68, as well as backings 69 and 70 are covered with electrically insulating plastic sheets 71 and 72 respectively, which are not thicker than 5% of the ultrasound wavelength used. The disclosed lead assembly comprises helically wound coaxial lead conductors and a stylet channel in a typical design for permanent leads. A simpler design is possible using standard insulated copper wires in a plastic tube which is typical design for disposable temporary pacing leads.

Figure 9:
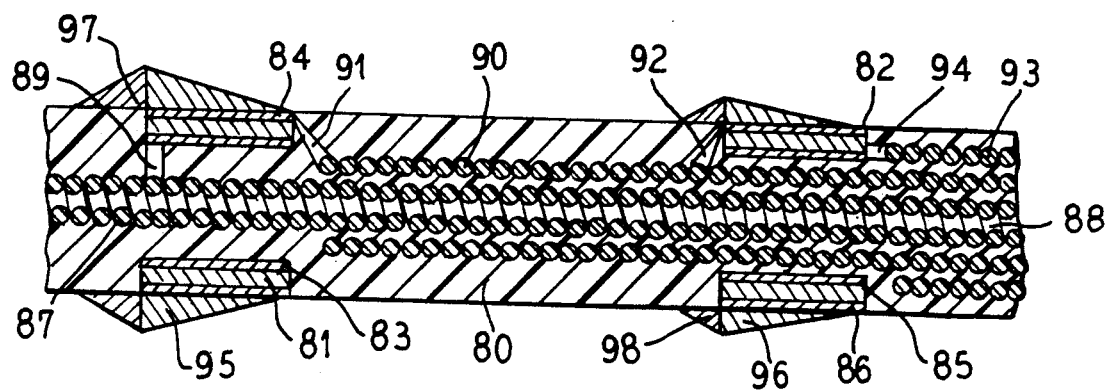
FIG. 9 is an axial cross-sectional view of the segment of the unipolar cardiac pacing lead comprising radially polarized transducers for continuous wave flow measurement.

In the embodiment of FIG. 9, there is disclosed a flow measurement assembly of the continuous wave flow measurement pacing lead. The lead comprises a plastic body 80 and piezoelectric transducers 81 and 82 which are embedded within the body 80. Transducer 81 is poled radially by means of electrodes 83 and 84, While the transducer 82 is poled radially by means of electrodes 85 and 86. Transducers 81 and 82 can be made in cylindrical form, or can be made as a folded piezoelectric plastic form (PVDF type). The inner lead conductor 87 having a stylet channel 88 is terminated on its distal end with a pacing electrode (not shown) and on its proximal end with a connector pin (not shown) as part of a connector assembly (not shown). Conductor 87 is electrically connected with electrode 83 by means of a conductive bridge 89. The middle coaxial lead conductor 90 is electrically connected to the electrode 84 by means of a conductive bridge 91 as well as to the electrode 86 by means of a conductive bridge 92. The outer coaxial lead conductor 93 is electrically connected to the electrode 85 by means of a conductive bridge 94. In such a way, electrical connections transducer 81 is connected to the external electronic circuits (not shown) through coaxial lead conductors 87 and 90 by means of said connector assembly (not shown) at the proximal end (not shown) of the lead. In the same manner the transducer 82 is connected to the external electronic circuits through coaxial lead conductors 90 and 93 by means of said connector assembly. The beam tilt needed for appropriate blood velocity measurement is achieved by using ultrasound lenses 95 and 96, as well as by means of reflective coatings 97 and 98.

Figure 10:
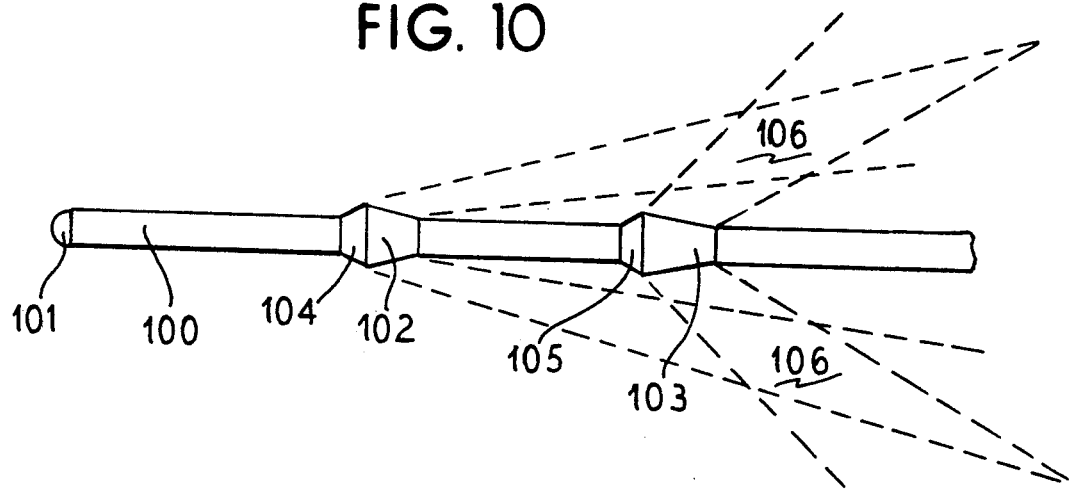
FIG. 10 is a view along the distal part of the lead such as shown in FIG. 9 disclosing the principle of ultrasonic radiation

In the embodiment of FIG. 10, there is a side view of the distal part of the continuous wave flow measurement pacing lead similar to that from FIG. 9 illustrating the ultrasonic beam tilt. The lead comprises a plastic body 100 having a pacing electrode 101 on the tip. The ultrasonic lenses 102 and 103 as well as reflective coatings 104 and 105 direct the sensitivity of transducers in such a way as it is illustrated by means of dashed lines which designate the geometric shape of the axial cross-section of the ultrasonic beams. The ultrasound beams of both transducers are axially symmetric and have geometric shapes of a top - cut hollow cone, in such a way as to avoid the intersection of ultrasonic beams with the lead itself. The geometric intersection of these two beams is a sensitivity volume axially symmetric with the axis of the lead, its axial cross-section 106 being two rhomboids. The blood velocity is measured within the sensitivity volume. The disclosed physical principle of the ultrasonic beams tilt and sensitivity volume as a beam intersection may be generalized for all continuous wave flow measurement leads, and also for the lead from FIGS. 6 and 8. The same geometrical shape of the ultrasonic beam is achieved by means of the transducer assembly from FIG. 7 and lead from FIG. 6 for use with PW Doppler systems. Furthermore, it is very important for CW as well as for PW Doppler leads that the ultrasonic beam is hollow in such a way as to prevent the intersection of the beam with the lead itself.

Figure 11:
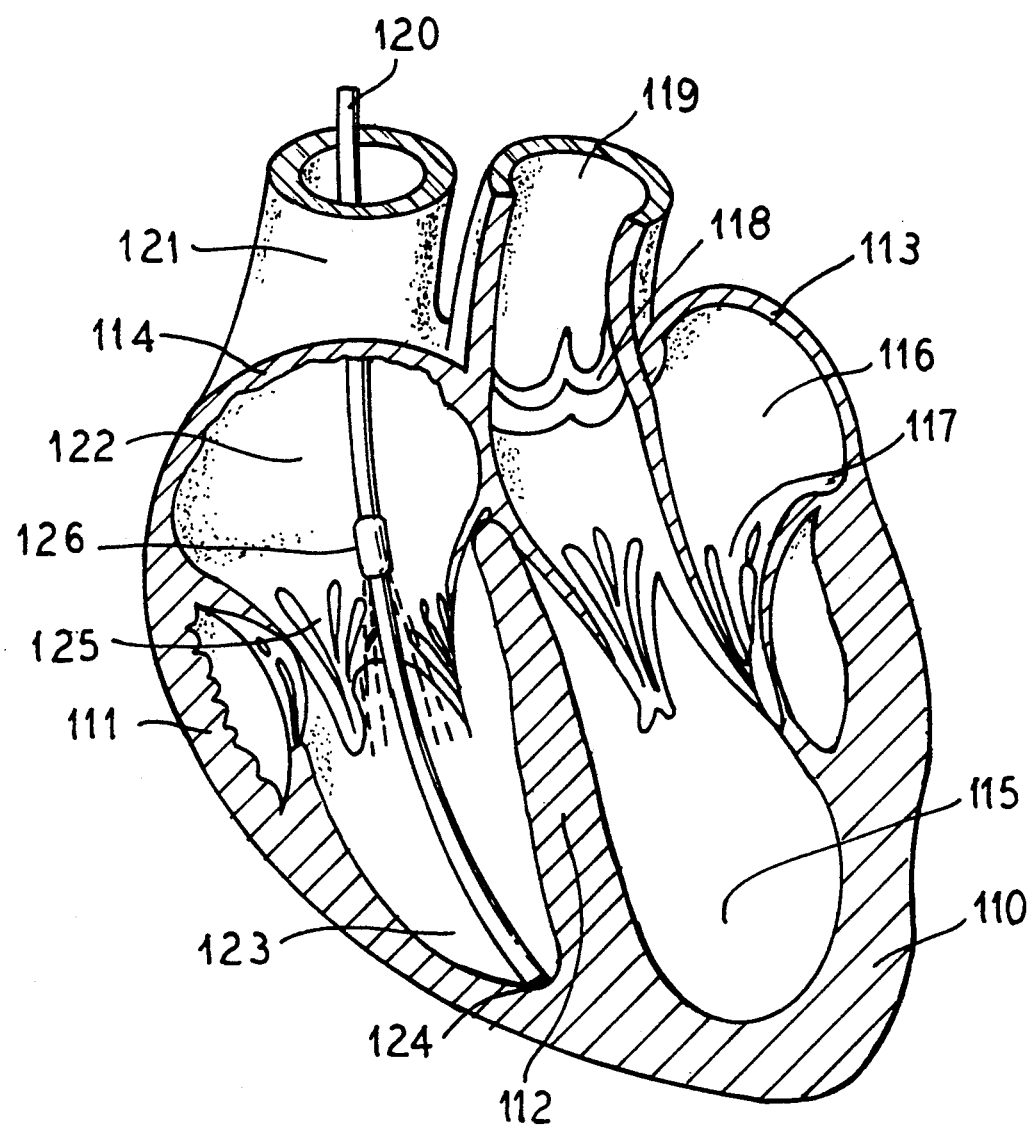
FIG. 11 is a cross-sectional four chamber view of the human heart showing approximately the anatomic structures and a cardiac pacing lead from FIGS. 5 and 7 implanted in the right portion of the heart.

In the embodiment of FIG. 11, the pulsed wave flow measurement pacing lead is shown within the anatomic structures of the human heart. The heart is disclosed in the four chamber cross-section, and the myocardial cross-section is visible for the left-ventricular wall 110, the right-ventricular wall 111, the interventricular septum 112, the left-atrial wall 113 and the right-atrial wall 114. Two chambers of the left heart, namely the left ventricle 115 and left atrium 116, are separated by the mitral valve 117. The left ventricular outflow tract consists of the aortic valve 118 and aorta 119. A cardiac pacing lead 120, such as disclosed in FIG. 5, is implanted through the vena cava superior 121 and the right atrium 122 in the right ventricle 123, with its pacing electrode 124 located in the apex of the right ventricle. In the lower right-atrial region above the tricuspid valve 125, the lead 120 comprises a flow measurement assembly 126 such as is disclosed in FIG. 7. Dashed lines emanating from the flow measurement assembly 126 designate the cross-section of the axially symmetric ultrasonic beam. The ultrasonic beam is directed in such a way as to enable the pulsed wave measurement of the blood flow through the tricuspid valve 125. Because the lead is bend in the rhythm of cardiac contractions, it is important that the ultrasonic beam does not intersect the lead which could provoke the distortion in the tricuspid flow pattern caused by movements of the lead.

Figure 12:
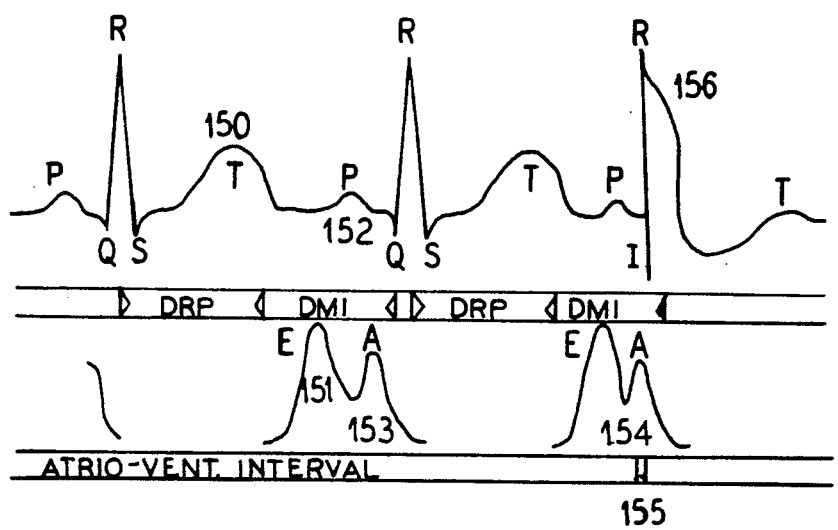
FIG. 12 is an illustration of a typical waveform of the pulsed Doppler blood flow measurement through the tricuspid valve, relative to the electrocardiogram.

In the embodiment of FIG. 12, an example of the electrocardiogram and corresponding pulsed wave Doppler waveform is disclosed. P waves, QRS complexes, and T waves are designated illustrating a normal ECG. The envelope of the pulsed wave Doppler waveform through the tricuspid valve is disclosed under the ECG in exact time correlation to the ECG. Important timing intervals are designated like Doppler refractory period (DRP), Doppler measurement interval (DMI) and atrio-ventricular interval. After the repolarization of the heart which caused the T wave 150, the relaxation of the heart muscle causes the early diastolic filling wave 151 having the peak blood velocity E. The following atrial depolarization causes the P wave 152 and corresponding atrial muscle contraction which pumps additional blood quantity producing the blood flow wave 153 having a peak velocity A. The ratio of peak velocities E/A is a hemodynamic parameter showing the cardiac muscle performance. The same Doppler waveform is obtained when measuring the mitral valve flow where peak velocities are having greater values (in order of 1 m/s), in comparison with tricuspid valve velocities being half slower. Another hemodynamic parameter being used in clinical practice is the ratio of the time integrated wave E and the time integrated wave A. The example is given for the healthy human heart, but pathologic conditions may disturb these relationships. This is used in this invention for diagnostic purposes. First of all, synchronized pacing is obtained in this invention by means of sensing the Doppler A wave and synchronizing the ventricular pacing with it, and not with the endocardial P wave as it is done in conventional VDD pacing systems. This is illustrated in the last complex where a following A-wave (154) is sensed and the atrio-ventricular interval (155) is initiated (shown as a black bar). At the end of the A-V interval, the pacing impulse I is generated, producing the paced R-wave 156. It is obvious that A-V intervals in this system are much shorter than in systems which sense the atrial electrogram. In the case of atrial fibrillation, the Doppler A waves disappear and this is used for atrial fibrillation detection. In the case of several ventricular arrhythmia like ventricular tachycardia and fibrillation, E waves disappear because the missing ventricular contraction causes missing ventricular relaxation. This is used for reliable life threatening arrhythmias detection. Any ischemic episode like pacing induced high rate ischaemia will change the ratio of peak velocities as well as the ratio of time integrals. This is used for physiologic maximum tracking rate response to prevent angina pectoris. The E/A ratio is significantly decreased in the case of a ventricular premature contraction without the compensatory pause. Circulatory catecholamines directly influence the interval between the QRS complex and the corresponding following Dippler E wave as well as they influence the rate of diastolic filling. Therefore, the sensors for rate responsive pacing are available in this system.

Figure 13:
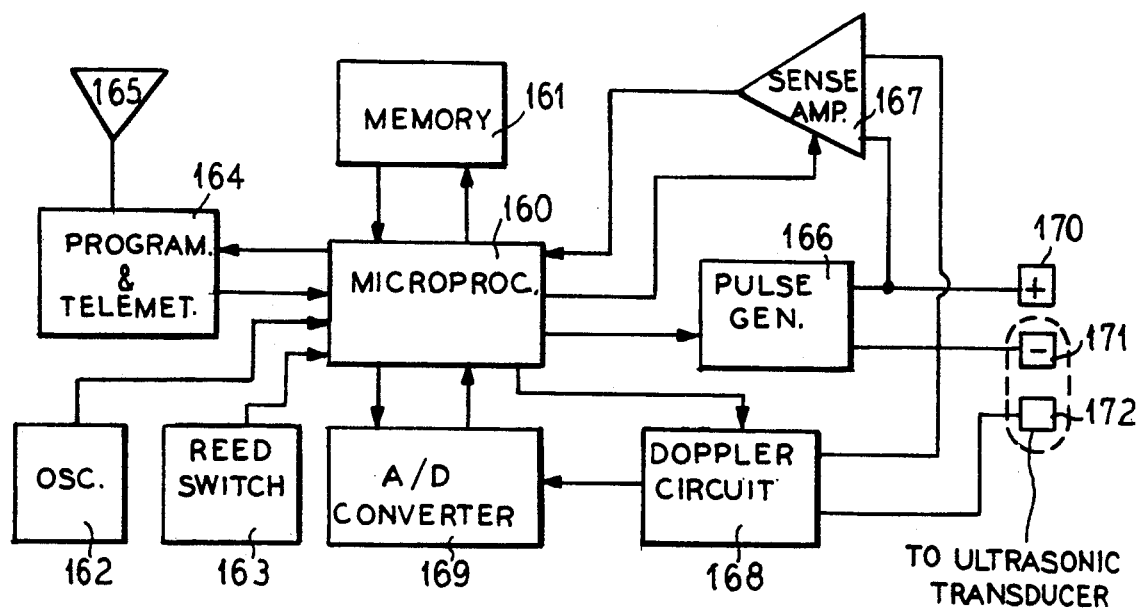
FIG. 13 is a simplified block diagram of a pacemaker comprising the pulse Doppler flow measurement circuit.
Figure 14A:
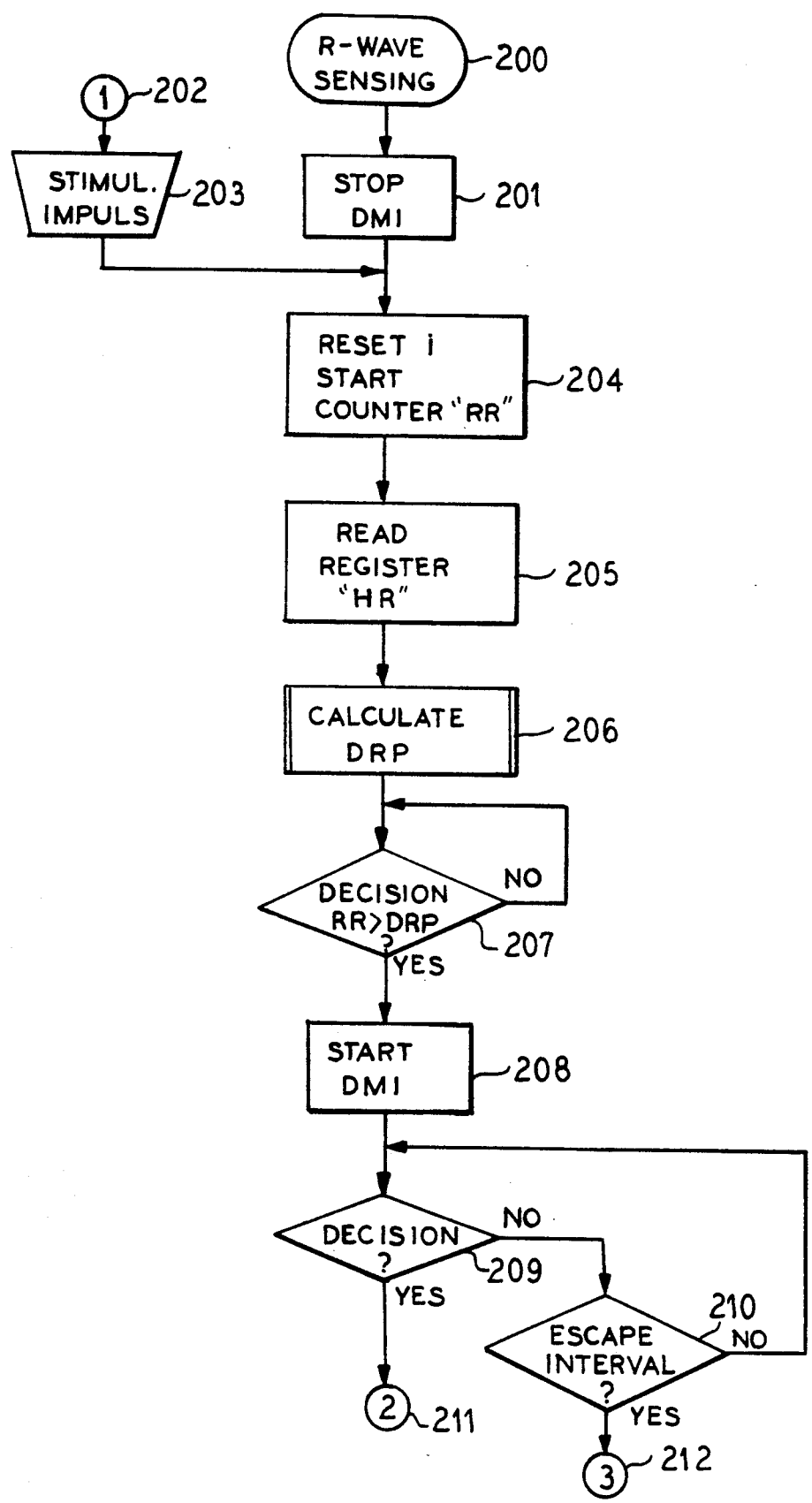
FIGS. 14A-14D is a flow chart illustrating the logical function of a pacemaker from FIG. 13.
Figure 14B:
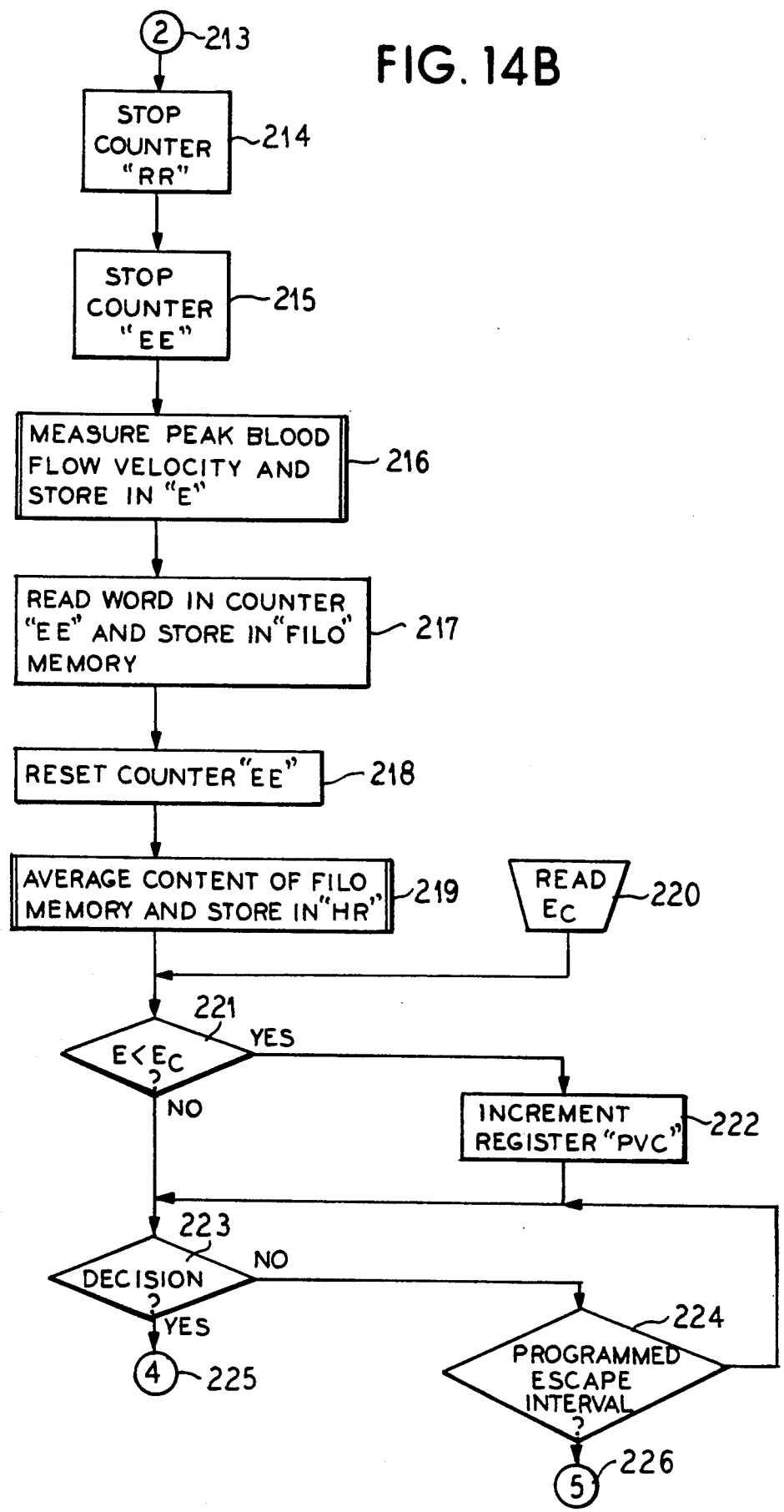
Figure 14C:
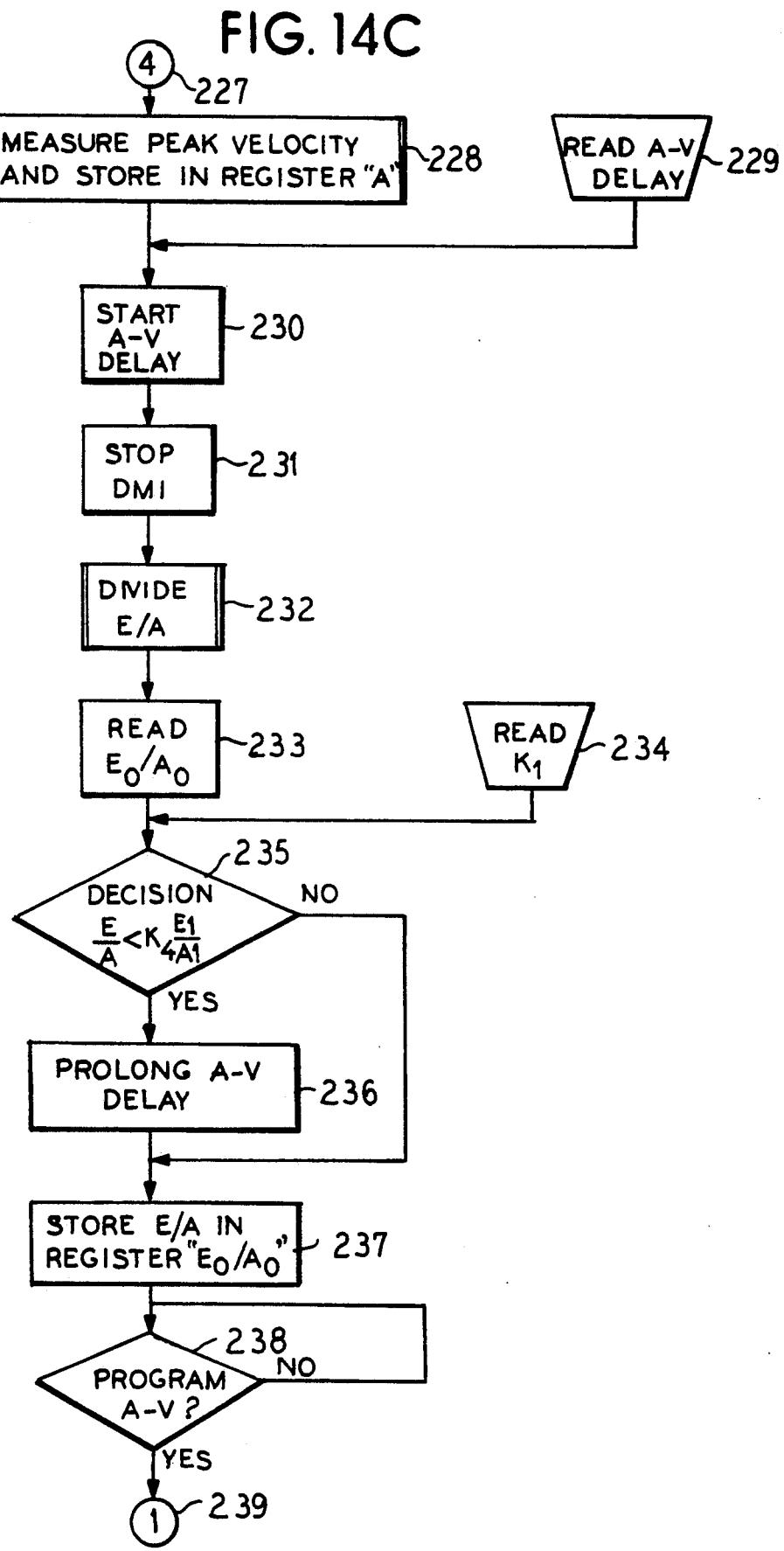
Figure 14D:
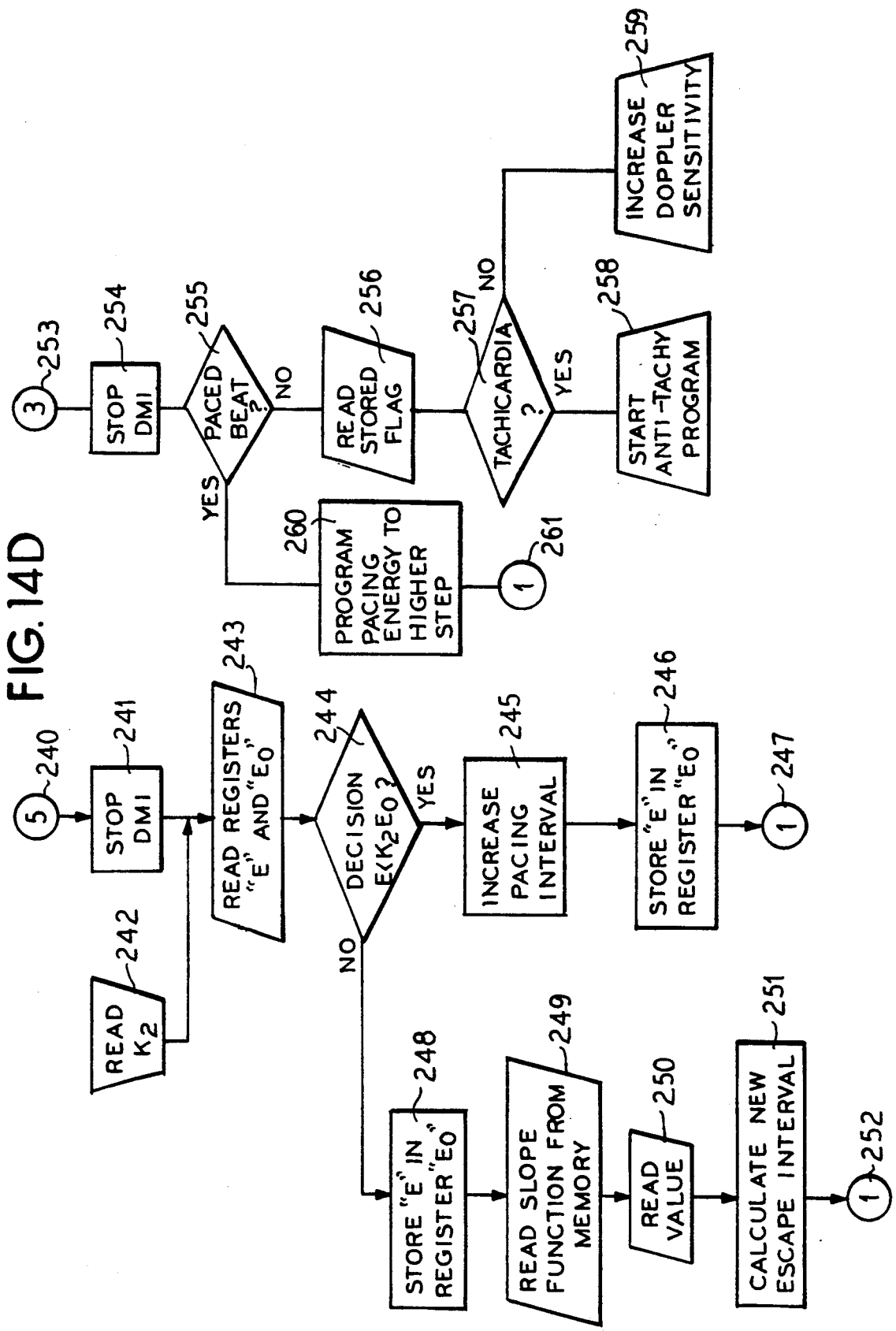

In the embodiment of FIG. 13, a generalized block diagram of a microprocessor controlled unipolar pacemaker is disclosed. Microprocessor 160 comprises a memory 161 where various data are kept in registers and counters generated by the software. Crystal oscillator 162 is producing an exact time base, and reed switch 163 may produce various functions known in the art. The implantable unit must be programmable by means of an external programmer and various telemetric functions are desirable. These functions are obtained by the programming and telemetry circuit 164 and radio-frequency communications circuit 165 with an antenna. The output pacing circuit 166 comprises a programmable pulse generator, voltage doubler, and protection circuit as it is known in the art. The programmable gain bandpass filter-amplifier 167 senses the endocardial ventricular signal picked up by the electrode during spontaneous ventricular heart beat. Doppler circuit 168 detects and measures the blood flow, and the analog-to-digital converter circuit 169 prepares the envelope of the Doppler waveform for digital processing. The positive pole of the pulse generator in circuit 166 and one pole of sensing amplifier 167 is connected to the pacemaker can at 170. The negative pole of the pulse generator in circuit 166 and another pole of the sensing amplifier 167 is connected to the pin 171 of a bipolar connector assembly. Pin 171 is electrically connected to the active pacing electrode in the ventricle and to the ultrasonic transducer when the lead such as disclosed in FIGS. 5 and 7 is coupled to the connector assembly. Another terminal of Doppler circuit 168 is connected to the pin 172 of a bipolar connector assembly being connected to the ultrasonic transducer of the lead such as is described in FIGS. 5 and 7. The disclosed system may have a unipolar pacing and sensing function through the pacemaker can 170 and connector pin 171, as well as Doppler measurements through the connector pins 171 and 172. The Doppler circuit may be designed to operate in the PW mode or in the CW mode. For the PW mode one can use lower frequencies (down to 2 MHz) with the range gate set to a near distance (up to 1.5 cm). In the CW mode the system operates at frequencies above 5 MHz, preferably at more than 8 MHz, reducing the effective range to the necessary value. The data are measured at characteristic phases of the cardiac cycle, i.e. in diastole, thereby saving energy from the pacemaker power source. The data collected in this way are fed into the pacemaker microprocessor and the data are then used for controlling the pacemaker. The Doppler electronic circuit can measure blood flow velocity using the Doppler effect, and the data to yield pulsativity and flow figures for pacemaker control. It can also measure the peak velocity as well as the time integral of the Doppler flow waveform envelope. The disclosed system comprises the connector assembly which is intended for use with a pulsed wave Doppler lead for unipolar pacing. A more complicated connector must be used in the continuous wave system as well as in the bipolar pacing system. The disclosed system can be incorporated in the implantable defibrillator-cardioverter as a pacing back-up system as well as a reliable system for fibrillation detection.

In the embodiment of FIGS. 14A-14D, a generalized flow-chart discloses one of many possible modes how the microprocessor polls various circuits in order to logically connect the function of Doppler blood flow measurement and cardiac pacing. Other possible functions of a microprocessor such as a tachycardia detection algorithm, electromagnetic interference response, programming, telemetry interrogation, and many other basic functions are not shown because these are well known in the art and are not the subject of this application. Sensing (200) of the spontaneous R-wave starts the routine and stops (201) the Doppler measurement interval DMI, which is the time during which the Doppler circuit is enabled for detection and measurement. A logical diagram connector is designated by (202) leading to the triggering (203) of the pacing impulse. In this example, the rate responsive sensor is the QE interval which is the time interval from either the paced or sensed QRS complex to the corresponding Doppler E wave. Therefore, the measurement of this interval is started (204) by resetting the counter "RR". The Doppler circuit is enabled after a certain delay from the QRS complex, which is called the Doppler refractory period (DRP). The DRP duration depends on the heart rate and becomes shorter as the heart rate increases and vice versa. Therefore, the heart rate is read (205) from the memory register "HR" and the DRP is calculated (206) according to the predetermined relation. This calculation may be in units of the "RR" counter, and upon the DRP termination (209) the DMI is started (208). The microprocessor waits (209) for the occurrence of the E wave as long as is the programmed escape interval (210). Logical diagram connectors are designated by 211, 212 and 213. Any first Doppler wave will be assigned as an E wave and upon occurrence (211), several actions will be initiated (213). The counter "RR" is stopped (214), now containing the QE interval duration. The counter "EE" is also stopped (215), now containing the interval between the former and the latter E wave, which is the numerical inverse of the actual heart rate. Doppler circuit measures (216) the peak blood flow velocity and stores its value in the memory register "E". The word in counter "EE" is read (217) and stored in a "First In Last Out" (FILO) type memory register, and the counter "EE" is reset (218) and starts to measure the next E to E wave interval. The DRP is calculated (206) according to the average heart rate during the last several heart beats. Therefore, the content of the FILO memory register is averaged (219) and the result is stored in the memory register "HR". The capacity of FILO, i.e. the number of FILO register words, is equal to the number of last beat to beat intervals which are averaged for the average heart rate, i.e. the content of register "HR". The microprocessor checks if the heart beat is with or without compensatory pause, thus enabling classification of the premature ventricular contractions (PVCs) without the compensatory pause. These kinds of PVCs produce significantly lower peak velocity of the early ventricular filling in comparison with the normal beat and PVCs with compensatory pause. Therefore, the preprogrammed critical peak velocity Ec is read (220) from the memory and compared (221) with the measured peak velocity stored in register "E". If there was a decrease of the rate of early diastolic filling, the beat is considered to be a PVC without compensatory pause, and the memory register "PVC" is incremented (222). The "PVC" memory register keeps the number of PVCs for later interrogation by the programmer for diagnostic purposes. The software routine may now enter the waiting loop for the second Doppler wave (223) which may last until the end of the programmed escape interval (224). The second wave is considered to be the atrial filling A wave. If the A-wave occurs, the software will continue to the synchronized pacing routine (225). If the A-wave is missing, the microprocessor considers that atrial fibrillation has occurred, and the rate responsive pacing routine will proceed (226).

Logical diagram connectors are designated by 225, 226, 227, and 239.

The routine continues (227) with the measuring (228) of the peak velocity which will be stored in the memory register "A". The preprogrammed value of atrio-ventricular delay is read (229) from the memory and the microprocessor initiates the A-V delay (230). In the meantime the DMI is stopped (23;) because there is no further Doppler wave expected. The content of memory register "E" is divided by the content of memory register "A" (232) in order to obtain the ratio of peak velocities of early diastolic and atrial filling. The same ratio of the former heart beat is read (233) from the memory register Eo/Ao. If the E/A ratio of the latter heart beat is significantly smaller (235) from the E/A ratio of the former heart beat, this means that the high rate ischemia is provoked and the angina pectoris may occur. The preprogrammed constant K1, read (234) from the memory, determines what is the significant change of the E/A ratio. In the case of high pacing rate ischemia, the A-V delay will be prolonged (236) in order to provoke the Wenckebach tracking rate response. It is known from the art that other maximum tracking rate responses are possible like 2:1 black as well as the fallback rate pacing. If there is no change in the E/A ratio, the value of the latter E/A ratio is stored (237) in the memory register Eo/Ao for future comparison with the next heart beat. The A-V delay waiting loop is entered (238) and the pacing pulse will be generated (239, 202) at the end. In the case of atrial fibrillation (226), the pacemaker will be programmed (240) to the rate responsive mode. The DMI is stopped (241) and the preprogrammed constant K2 is read (242) from the memory. Peak early diastolic velocities are read (243) from the register "Eo" for the former heart beat and from the register "E" for the latter heart beat. The high rate pacing induced ischemia will be always preceded by the drop of the early diastolic filling velocity. Therefore, the protection algorithm from high rates especially for patients with angina pectoris must be incorporated. The constant K2 determines the amount of beat to beat change of the peak velocity E. If the velocity E of the latter beat is significantly lower (244) than the velocity Eo of the former beat, the escape interval, i.e. the pacing interval in the rate responsive mode, must be increased (245). The latter peak velocity E is stored (246) in register Eo for future comparison with the next beat peak velocity. After that, the pacing impulse may be generated (247). If there is no significant change (244) in peak velocity, the value E is stored (248) in register "Eo" for future comparison with the next beat peak velocity. The programmed rate responsive slope function is read (249) from the memory and, according to the rate responsiveness sensor value stored in the counter "RR" (250), the new escape interval is calculated (251) and the pacing impulse is generated (252).

If there has been no first wave detected (209) and the escape interval was completed (212), the DMI is stopped (254). The microprocessor "knows" whether the expected Doppler wave had to be the consequence of the paced or the sensed beat. If this was a sensed beat (255), the flag which is influenced by the ventricular tachycardia and fibrillation detection algorithms is read (256). If the fibrillation or ventricular tachycardia was detected (257), it is a life threatening arrhythmia, and the anti-tachycardia subroutine is started (258), which may be defibrillation in an implantable defibrillator, or any other kid of anti-tachy therapy with an implantable device. If there was no tachycardia detected (257), the missing Doppler wave may be caused by the lack of Doppler circuit sensitivity. Therefore, the Doppler circuit sensitivity is increased (259). If this was a paced beat (255), the missing Doppler wave may be caused by the loss of capture. Therefore, the pacing output energy is reprogrammed to the higher step (260) and the pacing pulse is generated (261). Logic diagram connectors are designated by 240, 247, 252, 253 and 261. The disclosed logic diagram illustrates the function of a pacemaker only for the example of a basic idea. The function of the described invention in an external temporary pacemaker and in an implantable defibrillator has not been discussed in detail because the basic principle is the same with appropriate modifications as it is known in the art. For instance, there is no figure in this disclosure which shows the intracardiac spring lead for an implantable defibrillator, but it is obvious that Doppler transducers may be incorporated in such a lead, keeping the right design rules in mind.

Figure 15:
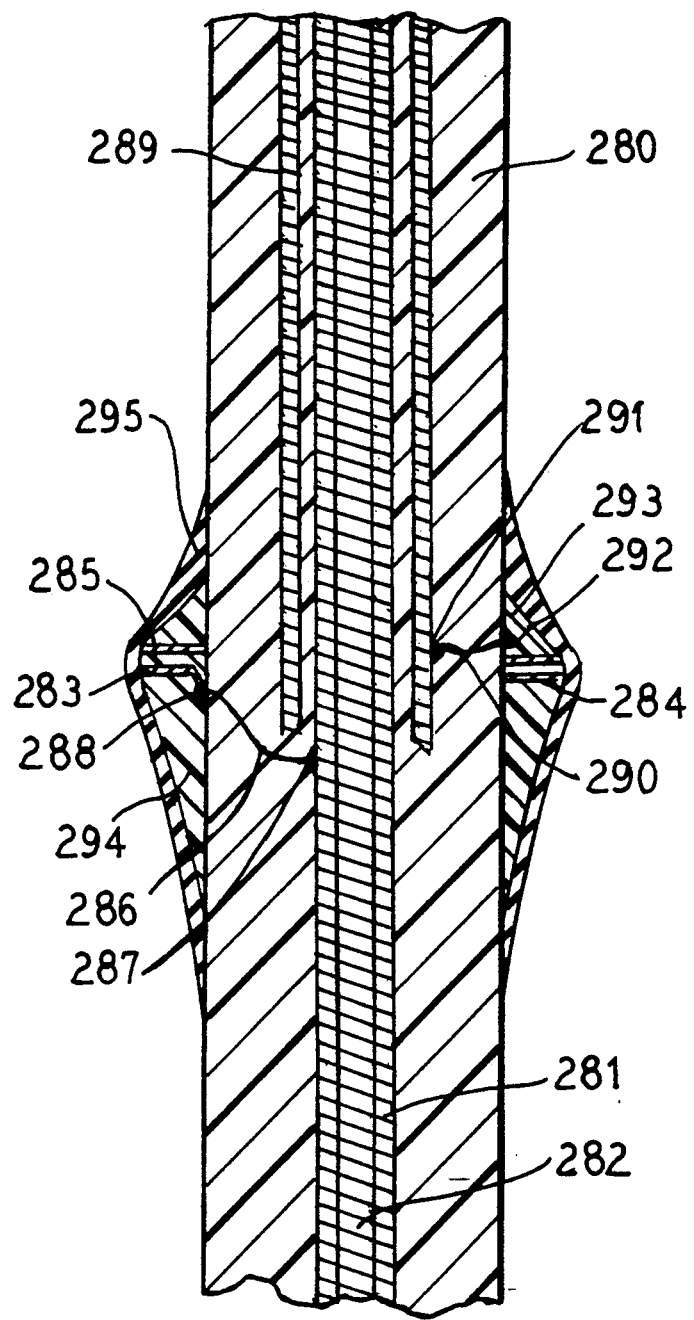
FIG. 15 shows a detailed axial cross-section of a lead and flow measurement transducer made of piezo film, either from the lead from FIG. 5 or from the distal transducer of the lead from FIG. 6.

In the embodiment of FIG. 15, there is disclosed a detailed axial cross-section of a lead and a flow measurement transducer made of piezo film, either from the lead from FIG. 5 or from the distal transducer of the lead from FIG. 6. Within the plastic body 280 there is a lead conductor 281 having a stylet channel 282 which connects the pacing electrode at the distal end (not shown) with the connector at the proximal end (not shown) of the lead. The piezoelectric transducer 283 made of material such as Kynar Piezo Film (Penwalt Corp.), mounted coaxially on the plastic body 280, has two electrodes 284 and 285, i.e. thin metallized layers. The transducer electrode 284 is electrically connected with the pacing lead conductor 281 by means of the connection wire 286 and electrical junctions 287 and 288. The transducer electrode 285 is electrically connected with another lead conductor 289 by means of another connection wire 290 and electrical junctions 291 and 292. An ultrasonic lens 293 is fitted and glued by the transducer. The lens 293 is of the form of a tapered ring and represents an essentially conical ultrasonic lens. At the end opposite to the lens of the transducer there is a backing 294 glued onto the electrode 284. The backing 294 is constructed of either an air equivalent material such as an expanded plastic, or of an ultrasound absorbing material such as a synthetic resin filled with metal powder. This backing is of such a tapered form that it does not obstruct the indwelling procedure. The lens 293, the transducer 283 and the backing 294 are covered with a thin sheath 295 of electrically insulating material not thicker than 5% of the ultrasound wavelength used.

The disclosed lead assembly comprises helically wound coaxial lead conductors with a stylet channel which is the technology used in leads for permanent implantation. A simpler design is possible for temporary cardiac leads using ordinary insulated copper wires in a plastic tube. The plastic body may consist of multiple insulation sheaths, i.e. plastic tubes between and over the lead conductors.

Another embodiment of the Doppler measurement device mounted at the point of interest on a cardiac pacing lead comprises plate transducers. The transducers are mounted on a tilted backing made of very ultrasound reflective material. The transducers are pairwise tilted out of the axial symmetry direction so that their directivities intersect, thus creating two sensitive volumes for continuous wave Doppler measurements. Unlike axially symmetric ultrasound sensitive volumes described in this patent application, this embodiment has two distinct sensitive volumes positioned at 180° across the catheter axis. The design, applicable for temporary pacing leads, is illustrated in FIGS. 16 to 19.

Figure 16:
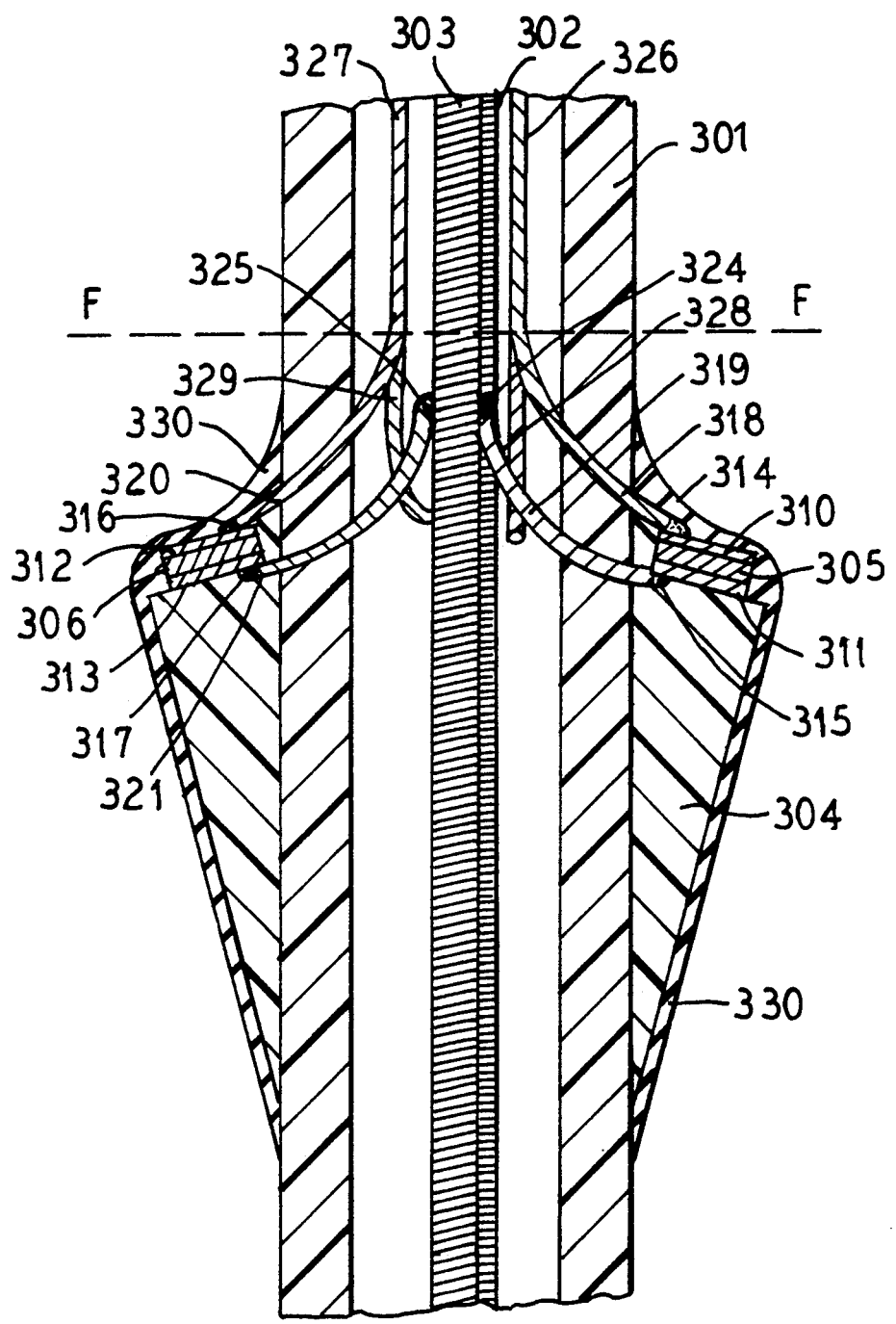
FIG. 16 is an axial cross-section through a bipolar pacing lead comprising plate transducers for velocity measurement.

FIG. 16 is an axial cross-section through a bipolar pacing lead comprising plate transducers for velocity measurement, mounted at an appropriate distance from the lead tip. The lead comprises:
a plastic hollow catheter body (301) within which there are pacing-sensing lead conductors (302 and 303) which are electrically connected to the corresponding electrodes (not shown) at their distal end, and to the corresponding connector pins (not shown) at their proximal end,
a backing (304) made of air equivalent material (hard expanded plastic) in the form of double truncated cones,
a multitude of plate piezoelectric transducers (305 and 306) glued to a surface of the backing (304), the transducers having thin metallized layers which are transducer electrodes (310, 311, 312, 313),
two additional piezoelectric plate transducers (not shown) to achieve circular symmetry,
an additional lead conductor (326) for connection of transducers, said conductor being bifurcated in two conductors (318 and 328),
an additional lead conductor (327) for connection of transducers, said conductor being bifurcated in two conductors (320 and 329).

The connection conductor (318) is conductively glued or soldered by means of an electrical junction (314) to the transducer electrode (310), thus the lead conductor (326) is the first pole of transducer (305). The connection conductor (328) is connected to the adjacent transducer (not shown) in the same manner and for the same purpose. The connection conductor (320) is conductively glued or soldered by means of electrical junction (316) to the transducer electrode (312), this lead conductor (327) being the first pole of transducer (306). The connection conductor (329) is connected to the opposite adjacent transducer (not shown) in the same manner and for the same purpose. The connection conductor (319) is conductively glued or soldered by means of electrical junction (315) to the transducer electrode (311), as well as by means of electrical junction (324) to the lead conductor (303), this lead conductor (303) being the second pole of transducer (305). The connection conductor (321) is conductively glued or soldered by means of electrical junction (317) to the transducer electrode (313), as well as by means of electrical junction (325) to the lead conductor (303), this lead conductor (303) being the second pole of transducer (306).

The transducer assembly is covered by means of an insulating sheath (membrane) (330) of thickness less than 5% of the wavelength of the dominant employed ultrasound frequency covering the whole device.

Figure 17:
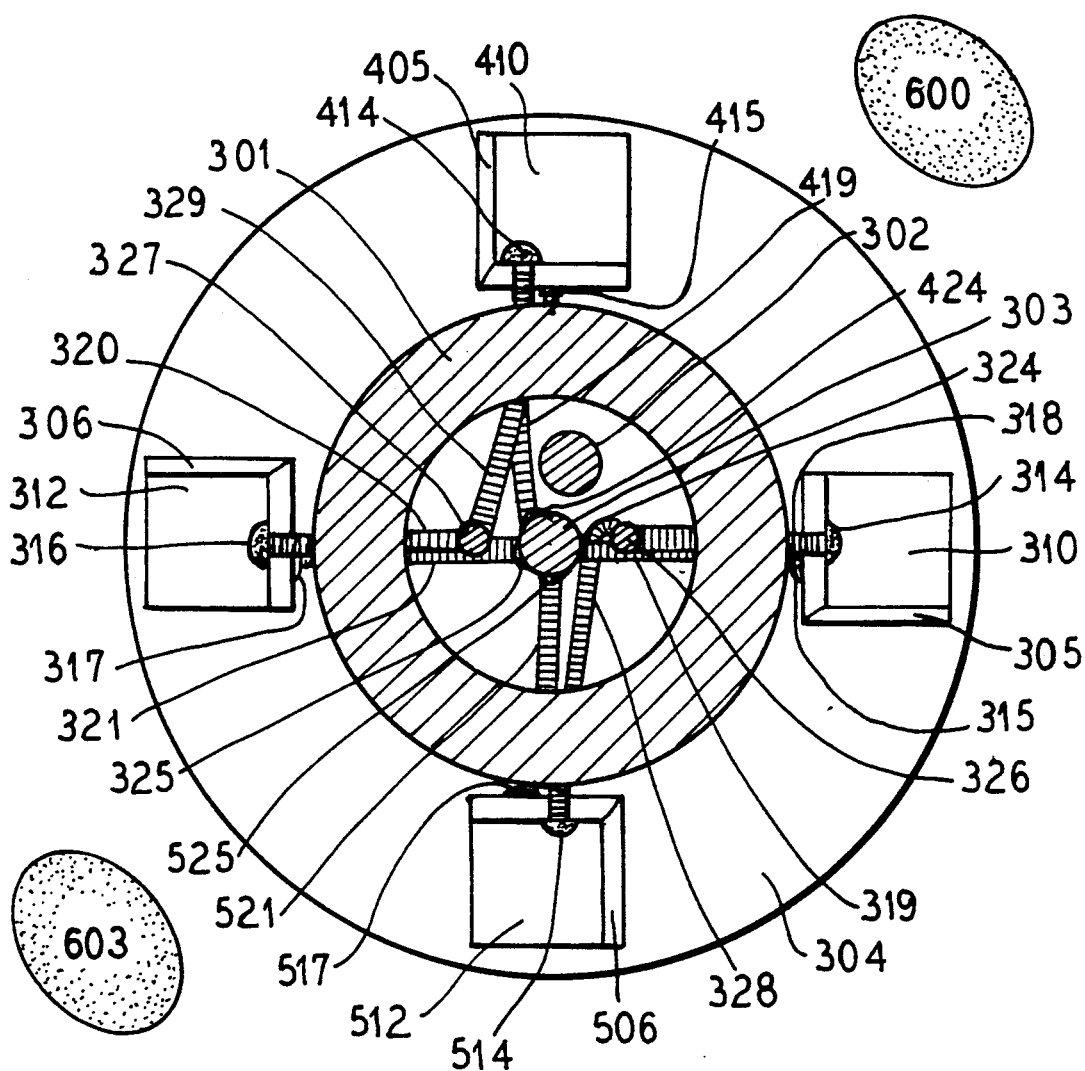
FIG. 17 is a transversal cross-section F—F as indicated in FIG. 16.

FIG. 17 is the transversal cross section F—F as indicated in FIG. 16. The device is shown without the insulating membrane (330). In this illustration one can see all the four plate transducers (305, 306, 405 and 506) having thin metallized layers (310, 312, 410 and 512, respectively). The opposite metallized layers cannot be seen from the disclosed view. These transducers are arranged in transmitter-receiver pairs, i.e. 306 and 506 are a pair, and 305 and 405 are a pair. The paired transducers are tilted towards each other, as can be seen by the perspective view of the transducer plates. The connection conductor 329 is connected to the transducer electrode 410 by means of the electrical junction 414, this conductor 327 being the first pole of transducer 405. The connection conductor 328 is connected to the transducer electrode 512 by means of the electrical junction 514, this conductor 326 being the first pole of transducer 506. The connection conductor 521 is connected to the transducer 506 through another metallized layer (not shown) by means of the electrical junction 517, and to the lead conductor 303 by means of the electrical junction 525, this conductor 303 being the second pole of the transducer 506. The connection conductor 419 is connected to the transducer 405 through another metallized layer (not shown) by means of the electrical junction 415, and to the lead conductor 303 by means of the electrical junction 424, this conductor 30 being the second pole of the transducer 405. In the disclosed wiring assembly, the lead conductor 303 is common for all four transducers. If the transmitter circuit is connected to lead conductor 326 and the receiver circuit to lead conductor 327 (or vice versa), transducers 305 and 506 will be ultrasonic transmitters, while transducers 306 and 405 will be ultrasonic receivers (or vice versa). The sideways tilt results in the overlapping of the directivity characteristics of the pairs of transducers as it is shown in the following figures. The perpendicular cross sections through the sensitivity areas at the level of section F—F are shown as shaded areas 601 and 602.

Figure 18:
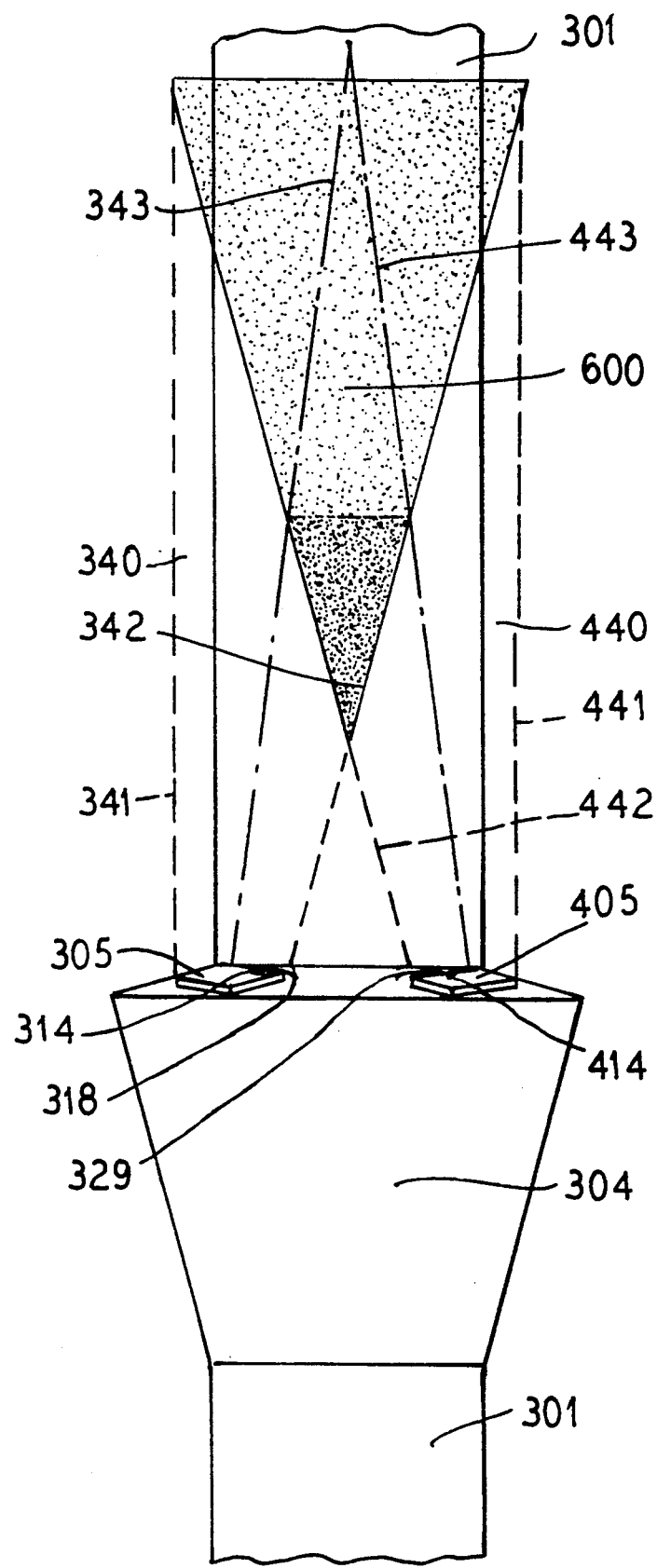
FIG. 18 is a perspective drawing of a side view of the lead from FIGS. 16 and 17.

FIG. 18 is a perspective drawing of the side view of the lead from FIGS. 16 and 17 without the covering insulation sheath (330) in order to illustrate the positions and tilts of the piezoelectric transducers (305 and 405) as well as the ultrasound directivity characteristics of the two transducers. The transducers are glued onto the air-equivalent backing (304). Their metallized layer electrodes are conductively glued or soldered by means of electrical junctions (314 and 414) to connection conductors (318 and 329, respectively). The connecting wires of other said transducers and the rest of the connecting Wires of transducers 305 and 405 are not shown. The body of the catheter (301) holds all the measuring devices, but can induce clutter into the ultrasonic measurement beams (340 and 440). The beams are illustrated by their boundaries—namely, boundaries 441 and 442 for transducer 405 and beam 440, and boundaries 341 and 342 for transducer 305 and beam 340. Directivity axis 343 is for transducer 305 and beam 340, and directivity axis 443 is for transducer 405 and beam 440. The overlapping region between the beams 440 and 340 is indicated as well (600). When the two transducers (305 and 405) act as a Doppler transmitter-receiver combination, the overlapping region (600) is the sensitive area of the blood flow velocity measurement. Disclosed boundaries are drawn for illustration only and they can be exactly defined as a surface of specified ultrasonic field intensity.

Figure 19:
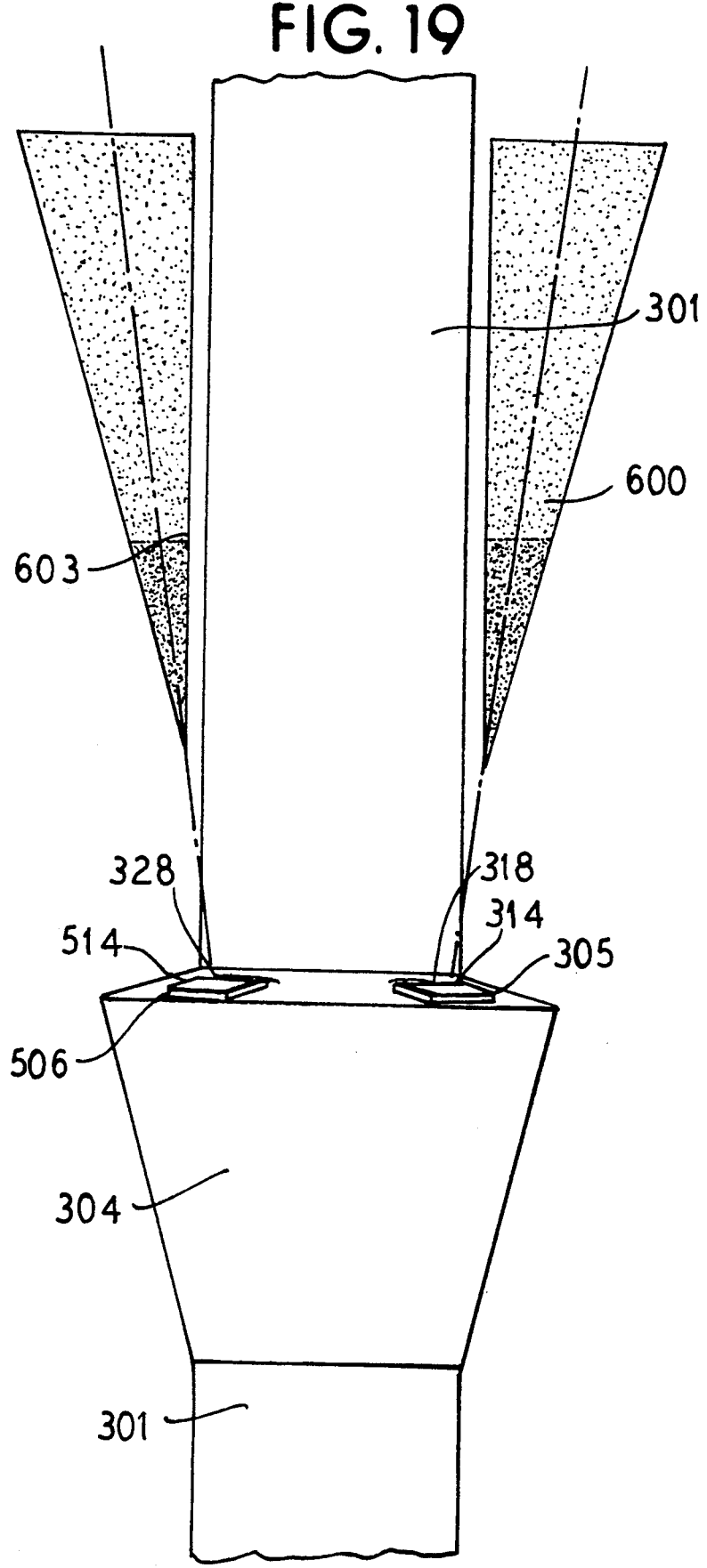
FIG. 19 illustrates the situation of FIG. 18 only, shown from an angle of 90° around the catheter axis.

FIG. 19 illustrates the situation of FIG. 18 only, shown from an angle of 90° around the catheter axis. This illustration shows that, while there is an overlapping zone between pairs of transducers as shown in FIG. 18, there is a dead zone of sensitivity at positions at 90° around the axis to the sensitive area positions. Two opposite sensitivity volumes 600 and 603 are disclosed. The former is the geometrical intersection of ultrasonic beams of transducers 305 and 405, while the latter is the geometrical intersection of ultrasonic beams of transducers 506 and 306. The disclosed transducer assembly produces two ultrasonic sensitive volumes in order to obtain more reliable blood velocity measurement. However, a simpler design is possible with only two transducers producing one sensitive volume.

While specific embodiments of the present invention have been described, it should be understood that these embodiments are described for purposes of illustration only. The foregoing description is not intended in any way to limit the scope of the present invention.

We claim as our Invention:

1. A cardiac electrotherapy system, comprising:

flow velocity measurement means for measuring velocity of blood flow at a region of a tricuspid valve between a right auricle and right ventricle of a heart;

pacing means for providing a pacing signal to the heart; and control means responsive to the measured blood flow velocity for controlling the pacing signals to the heart.

2. A system according to claim 1 wherein the flow velocity measurement means comprises a blood flow transducer and the pacing means comprises a pacing electrode, the transducer and electrode both being provided on a single cardiac pacing lead which is designed to be implanted into the heart such that the transducer is located at a region of the tricuspid valve and the pacing electrode is located in the right ventricle.

3. A system according to claim 2 wherein the pacing electrode is positioned at an apex of the right ventricle.

4. A system according to claim 1 wherein the flow velocity measurement means comprises an ultrasonic transducer.

5. A system according to claim 4 wherein the flow velocity measurement means includes a Doppler means for sending and receiving ultrasonic signals from the ultrasonic transducer for measuring blood flow velocity by Doppler measurements.

6. A system according to claim 1 wherein said control means comprises means for detecting a first peak velocity wave comprising a diastolic filling wave indicating relaxation of a heart muscle of the heart, and a second peak velocity wave comprising an atrial contraction wave indicating atrio muscle contraction.

7. A system according to claim 6 wherein a velocity peak of the first wave is higher than a velocity peak of the second wave.

8. A system according to claim 6 wherein the control means has means for synchronizing pacing with said second atrial contraction wave.

9. A system according to claim 6 wherein said control means includes means for forming a ratio of peak velocities of the first wave and the second wave for determining a cardiac irregularity.

10. A system according to claim 6 wherein said control means includes means for detecting severe ventricular arythmia by detecting a substantial decrease or absence of the first diastolic filling wave.

11. A system according to claim 6 wherein said control means includes means for analyzing cardiac muscle performance by determining a ratio of peak velocities of the first diastolic filling wave to the second atrial contraction wave.

12. A system according to claim 6 wherein said control means includes means for sensing ventricular tachycardia by analyzing the first diastolic filling waves for irregular peak velocity.

13. A system according to claim 6 wherein said control means includes means for detecting atrial fibrillation by checking for a substantial absence of the second atrial contraction wave.

14. A system according to claim 1 wherein said control means has means for detecting a peak of a flow velocity wave corresponding to atrial contraction and for providing a pacing signal synchronous with said flow velocity wave.

15. A system according to claim 1 wherein said control means includes means for sensing cardiac irregularity through analysis of peak velocity filling waves.

16. A system according to claim 1 wherein said control means includes means for detecting life threatening arrythmias by analyzing a change of a ratio of peak flow velocities.

17. A system according to claim 1 wherein said control means has means for analyzing flow velocity profiles for detecting atrial fibrillation, ventricular tachycardia, and ventricular fibrillation.

18. A system according to claim 1 wherein said control means has means for measuring blood flow velocity during a determined time interval which is synchronized with ventricular electrical activity.

19. A system according to claim 18 wherein the time interval occurs with a determined delay after ventricular activity.

20. A system according to claim 1 wherein said control means has means for discriminating between blood velocity profiles comprising an early diastolic filling wave and an atrial filling wave.

21. A system according to claim 20 wherein said discriminating means includes means for measurement of peak velocities of both waves and calculation of time integrals of both waves.

22. A system according to claim 1 wherein said control means includes means for ventricular pacing synchronous with a blood velocity atrial filling wave, and wherein said ventricular pacing maintains a physiologic atrio-ventricular delay.

23. A system according to claim 1 wherein said control means includes means for detecting a flow velocity diastolic filling wave and an atrial filling wave.

24. A system according to claim 23 wherein means are provided for calculation of a ratio of peak velocities and a ratio of time integrals of said diastolic and atrial filling waves.

25. A system according to claim 24 wherein said control means includes means for beat-to-beat comparison of said ratios in order to indicate a high rate induced ischemia, and means for a successive decrease of ventricular pacing rate so as to detect high rate ischemia and prevent a high rate induced cardiac ischemia.

26. A system according to claim 23 wherein said control means includes means for detection of atrial fibrillation indicated by disappearance of said atrial filling wave, means for maintaining a rate responsive ventricular pacing while the atrial fibrillation is sustained, and means to revert to synchronous ventricular pacing upon occurrence of said atrial filling wave.

27. A system according to claim 23 wherein said control means includes means for measurement of a time interval between a ventricular pacing impulse and said diastolic filling wave, and further including means for changing pacing rate when the interval changes.

28. A system according to claim 23 wherein said control means further includes means for measurement of a time duration of said diastolic filling wave, and further including means for changing a pacing rate when said duration changes.

29. A system according to claim 23 wherein said control means further includes means for measurement of a first derivitive at an onset of said diastolic filling wave, and means for utilizing said derivitive for changing pacing rate.

30. A system according to claim 23 wherein said control means includes means for determining peak velocities of said flow velocity diastolic filling wave and atrial filling wave and means being provided for changing a pacing rate when either of said peak velocities change.

31. A system according to claim 23 wherein said control means includes means for detecting a missing ventricular contraction by determining disappearance of diastolic filling waves, and further including means for discriminating if missing contractions are caused by loss of capture or by ventricular fibrillation.

32. A system according to claim 23 wherein said control means includes means for detecting a measured peak velocity of the diastolic filling wave for a single beat, and means for detecting a sudden decrease of said measured peak velocity indicating that said single beat is a ventricular premature beat.

33. A system according to claim 23 wherein said control means includes means for measuring a peak velocity of the diastolic filling wave for a series of heartbeats, and including means for determining a sudden decrease which is indicative of a series of beats corresponding to ventricular tachycardia.

34. A system according to claim 1 wherein said control means includes means for calculating a rapid filling fraction based on measured flow velocity and means for changing a pacing frequency when said filling fraction changes.

35. A system according to claim 1 wherein said flow velocity measurement means comprises means for measuring blood flow velocity with ultrasonic waves and which further includes means for Doppler blood flow velocity measurement, timing, and processing of velocity data.

36. A system according to claim 35 wherein said means for measuring blood flow velocity comprises a lead formed of a plastic body having at least .one ultrasonic piezoelectric transducer thereon.

37. A system according to claim 36 wherein the piezoelectric transducer has a cylindrical geometric shape and is mounted coaxially onto the lead and is poled lengthwise along a longitudinal axis of the lead with transducer electrodes at opposite ends of the piezoelectric transducer, said transducer having means for creating a substantially narrow, conical directivity characteristic around the lead so as to prevent intersection of an ultrasonic beam from the transducer with the lead when the lead is in a substantially straight alignment.

38. A system according to claim 36 wherein said lead has a pacing electrode at a distal end thereof spaced from the transducer, and a connector assembly at a proximal end thereof, and wherein lead conductors are provided in the plastic body which electrically connect the pacing electrode and said electrodes of the transducer with corresponding pins of the connector assembly.

39. A system according to claim 36 wherein said transducer has electrodes at opposite surfaces thereof and a reflector means fixed adjacent one of the transducer electrodes for preventing ultrasonic radiation in a direction of the side where the reflector means is mounted.

40. A system according to claim 36 wherein said transducer has electrodes at opposite surfaces thereof and has an absorbing means fixed adjacent one of the transducer electrodes for preventing ultrasonic radiation in a direction of the side where the absorbing means is mounted.

41. A system according to claim 36 wherein said transducer has electrodes at opposite ends thereof and has an ultrasonic lens means mounted adjacent to one of the transducer electrodes for directing ultrasonic radiation towards the side of the transducer where the lens is mounted such that an ultrasonic beam having a geometric shape of a top-cut hollow cone which is coaxial with a longitudinal axis of the lead is provided.

42. A system according to claim 41 wherein said lens is in the form of a tapered conical ring.

43. A system according to claim 35 wherein a single ultrasonic transducer is provided wherein said means for Doppler blood flow measurement comprises means for detecting and range gating a characteristic pulse wave Doppler waveform produced by blood flow through the tricuspid valve.

44. A system according to claim 35 wherein two spaced apart ultrasonic transducers are provided and said control means includes means for detecting characteristic continuous wave Doppler waveforms.

45. A system according to claim 35 wherein said means for measuring blood flow with ultrasonic waves comprises a cylindrical ring of piezo transducer material having a first electrode on an inside of the annular ring and a second electrode on an outside of the annular ring, and wherein beam tilt lens means is provided over the outside second electrode for tilting an ultrasonic beam into a conical pattern extending along a longitudinal axis of the lead, and wherein means for preventing a transmission of ultrasonic waves in a direction opposite to the direction of the conical pattern is positioned adjacent the tilt lens means.

46. A system according to claim 1 wherein said means for measuring blood flow with ultrasonic waves comprises an annular piezoelectric transducer surrounding an outer periphery of a plastic body containing lead conductors and wherein opposite sides of the annular transducer have thin metal layer electrodes thereon with wires connecting to the plastic body lead conductors, and wherein an ultrasonic lens means is provided in a conical shape along an outside periphery of the plastic body adjacent one of the electrodes and means for preventing radiation of ultrasonic waves is positioned adjacent the other electrode for preventing radiation of waves in a direction opposite to where the lens means is provided.

47. A system according to claim 1 wherein said flow velocity measurement means comprises at least first and second plate-like transducer means for ultrasonic waves mounted in spaced apart fashion and outwardly of a plastic lead having lead conductors therein for the transducer means, wherein electrodes are mounted on opposite sides of the plate-like transducer means with connection wires to the plastic lead conductors, and wherein said transducer means are positioned such that when one is transmitting and the other is receiving ultrasonic waves, an overlapping sensitive area region is created at one side of the plastic lead.

48. A system according to claim 47 wherein four of said plate-like transducer means are provided at equidistant positions around a periphery of the plastic lead wherein two of the transducer means form a transmitter/receiver pair and the other two transducer means provide another transmitter/receiver pair so as to define first and second sensitive area regions on opposite sides of the plastic lead, and with a dead zone at the periphery of the plastic lead between the two sensitive areas.

49. A cardiac electrotherapy system, comprising:
a cardiac pacing lead having a pacing electrode at one end within a ventricle of the heart and a flow velocity measurement means spaced from said pacing electrode and positioned for measuring a blood flow velocity at a valve between an auricle and said ventricle of the heart; and
first means in communication with said cardiac pacing lead for measuring and processing flow velocity waveforms, second means connected to said first means for detecting heart irregularities, and third means connected to said second means for pacing the heart when needed in synchronization with at least a portion of the flow velocity waveforms.

50. A system according to claim 49 wherein said flow velocity measurement means comprises a Doppler ultrasonic transducer means and connected means for measuring said flow velocity by Doppler technique.

51. A cardiac electrotherapy method comprising the steps of:
measuring velocity of blood flow at a region of a tricuspid valve between a right auricle and right ventricle of a heart;
pacing the heart with a pacing signal; and
controlling the pacing signal to the heart based on the measured blood flow velocity.

52. A cardiac electrotherapy method, comprising the steps of:
placing a cardiac pacing lead in a heart such that a pacing electrode at one end of the lead is positioned within a ventricle of the heart and a flow velocity measurement transducer spaced from the pacing electrode is positioned for measuring a blood flow velocity at a valve between an auricle and said ventricle of the heart;
measuring and processing blood flow velocity waveforms from the transducer for detecting heart irregularities; and
controlling a pacing of the heart when needed in synchronization with at least a portion of the flow velocity waveforms.

53. A method according to claim 52 including the step of measuring the flow velocity by a Doppler ultrasonic technique.

* * * * *